(12) United States Patent
Uchiyama et al.

(10) Patent No.: US 7,604,591 B2
(45) Date of Patent: Oct. 20, 2009

(54) CAPSULE MEDICAL APPARATUS

(75) Inventors: Akio Uchiyama, Yokohama (JP);
Hironobu Takizawa, Hachioji (JP);
Masatoshi Homan, Hiho (JP)

(73) Assignee: Olympus Corporation, Tokyo (JP)

( * ) Notice: Subject to any disclaimer, the term of this patent is extended or adjusted under 35 U.S.C. 154(b) by 744 days.

(21) Appl. No.: 10/974,486

(22) Filed: Oct. 27, 2004

(65) Prior Publication Data
US 2005/0154294 A1    Jul. 14, 2005

(30) Foreign Application Priority Data
Oct. 27, 2003  (JP)  ............... 2003-366575
Oct. 28, 2003  (JP)  ............... 2003-368045

(51) Int. Cl.
*A61B 1/00*  (2006.01)
*A61B 5/07*  (2006.01)

(52) U.S. Cl. ............... 600/130; 600/160; 600/302

(58) Field of Classification Search ............... 600/101, 600/160, 130, 407, 476; 343/895
See application file for complete search history.

(56) References Cited

U.S. PATENT DOCUMENTS

| | | | | |
|---|---|---|---|---|
| 3,783,417 A | * | 1/1974 | Osada et al. | ............... 333/185 |
| 4,278,077 A | | 7/1981 | Mizumoto | |
| 5,933,318 A | * | 8/1999 | Tomono et al. | ............... 361/323 |
| 6,201,387 B1 | * | 3/2001 | Govari | ............... 324/207.17 |
| 6,632,216 B2 | * | 10/2003 | Houzego et al. | ............... 604/890.1 |
| 7,001,329 B2 | * | 2/2006 | Kobayashi et al. | ............... 600/114 |
| 7,354,398 B2 | * | 4/2008 | Kanazawa | ............... 600/109 |
| 2002/0047812 A1 | * | 4/2002 | Otomo et al. | ............... 343/895 |
| 2002/0165592 A1 | * | 11/2002 | Glukhovsky et al. | ............... 607/62 |
| 2003/0060702 A1 | | 3/2003 | Kuth et al. | |
| 2005/0228259 A1 | * | 10/2005 | Glukhovsky et al. | ............... 600/407 |

FOREIGN PATENT DOCUMENTS

| | | |
|---|---|---|
| DE | 2929429 | 2/1980 |
| DE | 19740428 A1 * | 3/1999 |
| GB | 2280789 A * | 2/1995 |
| JP | 55-19124 | 2/1980 |
| JP | 07-246243 | 9/1995 |
| JP | 8-503384 | 4/1996 |
| JP | 2001-91860 | 4/2001 |
| JP | 2001-104241 | 4/2001 |
| JP | 2001-170002 | 6/2001 |

(Continued)

OTHER PUBLICATIONS

Ohishi, Tsukasa, et al., "Technology of High Density Multi-Chip System on Film (SOF)", Technical Journal Sharp (2002); vol. 83, pp. 16-18.
International Publication No. WO 9401165 A1—Abstract only.

*Primary Examiner*—John P Leubecker
(74) *Attorney, Agent, or Firm*—Scully, Scott, Murphy & Presser, P.C.

(57) ABSTRACT

A capsule casing is inserted into the living body, a thin-film substrate is cylindrically-shaped with approximately the same size of the inner surface of the casing and a coil for receiving an AC magnetic field is formed, and thus AC power is generated by the AC magnetic field from the outside of the living body with a small mounting space.

50 Claims, 22 Drawing Sheets

FOREIGN PATENT DOCUMENTS

| | | |
|---|---|---|
| JP | 2001-224551 | 8/2001 |
| JP | 2001-224552 | 8/2001 |
| JP | 2002-298095 | 10/2002 |
| JP | 2002-315209 | 10/2002 |
| JP | 2003-111720 | 4/2003 |
| JP | 2003-135389 | 5/2003 |
| JP | 2003-210395 | 7/2003 |
| JP | 2004/528890 | 9/2004 |
| WO | WO 02/080753 A2 | 10/2002 |
| WO | WO 03/071299 A1 | 8/2003 |

* cited by examiner

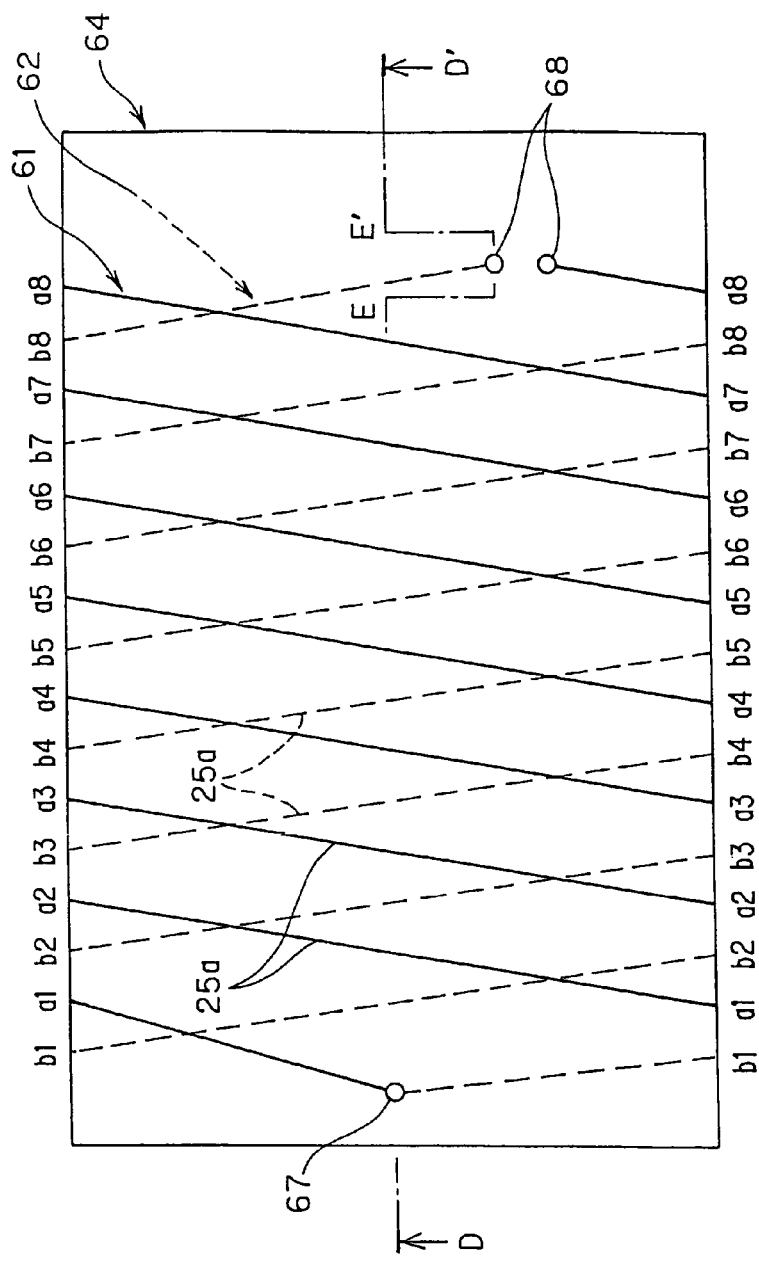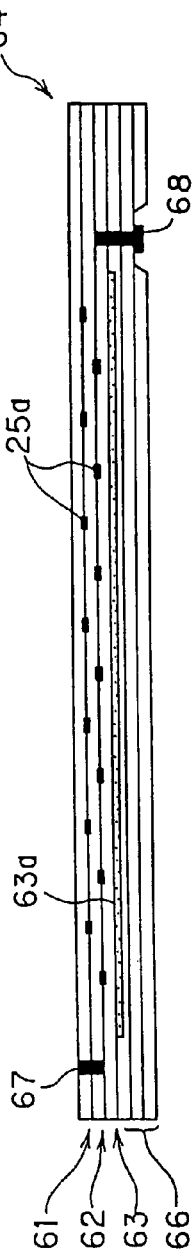
FIG.10A
FIG.10B

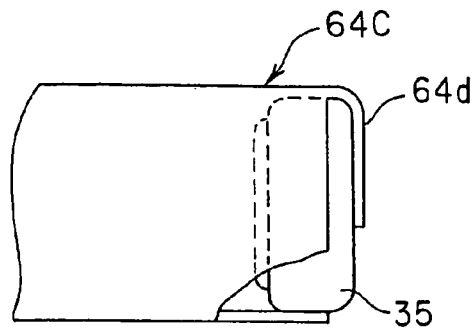
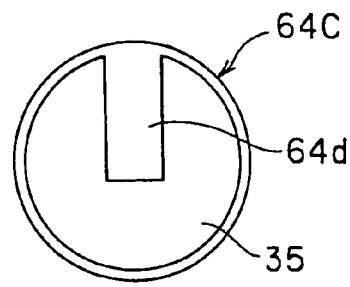
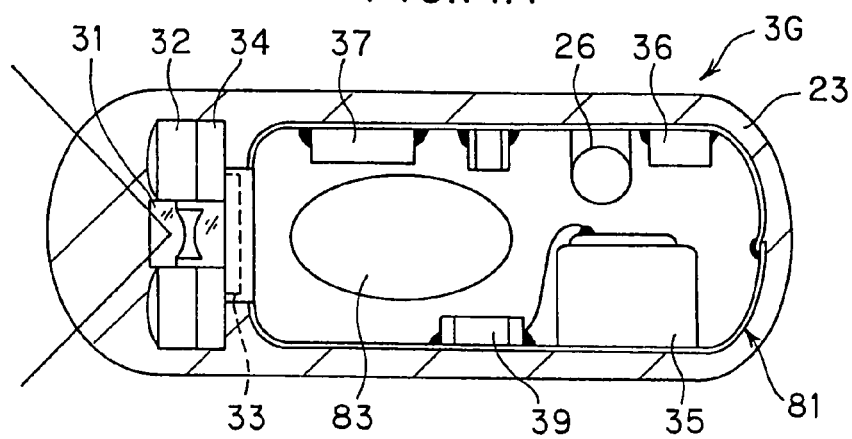
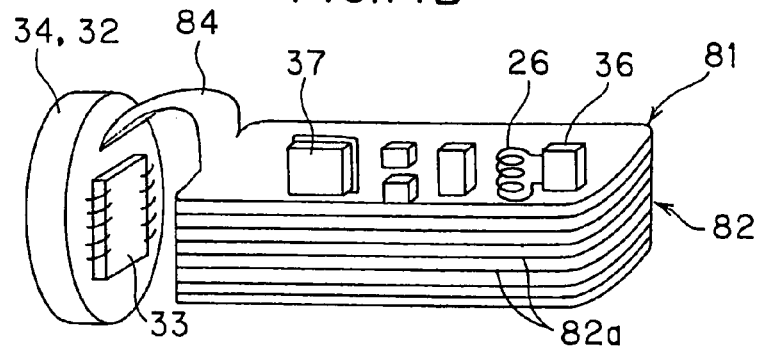
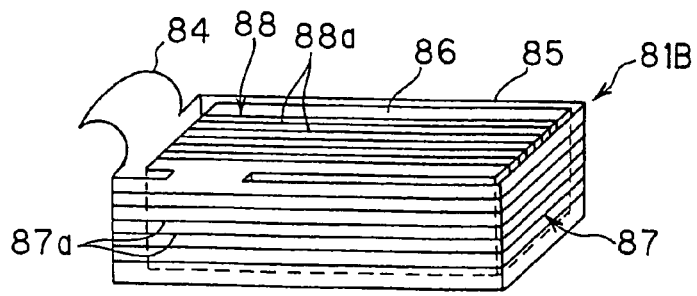

FIG.24A
FIG.24B
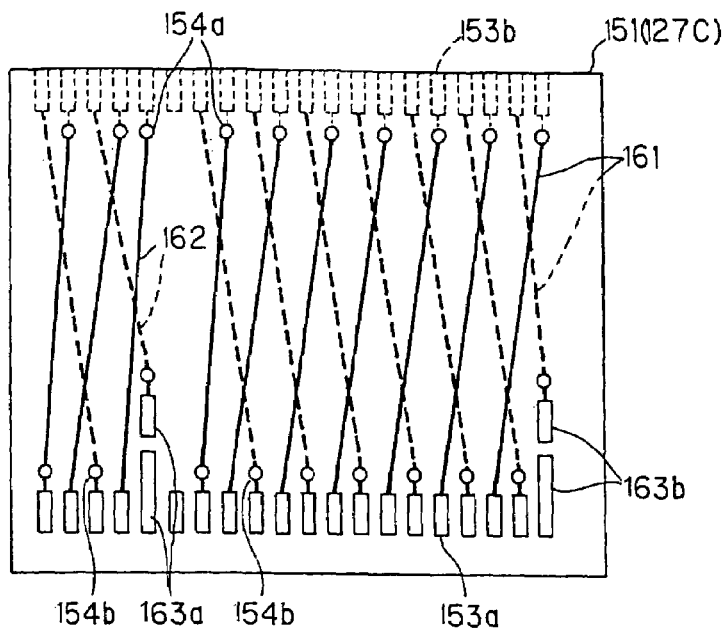
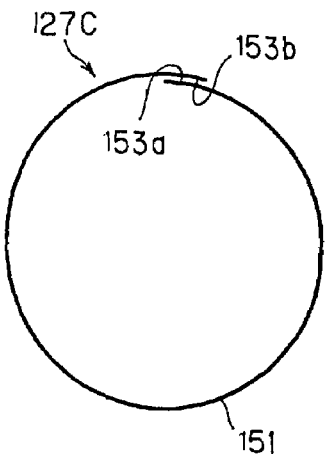
FIG.25A
FIG.25C
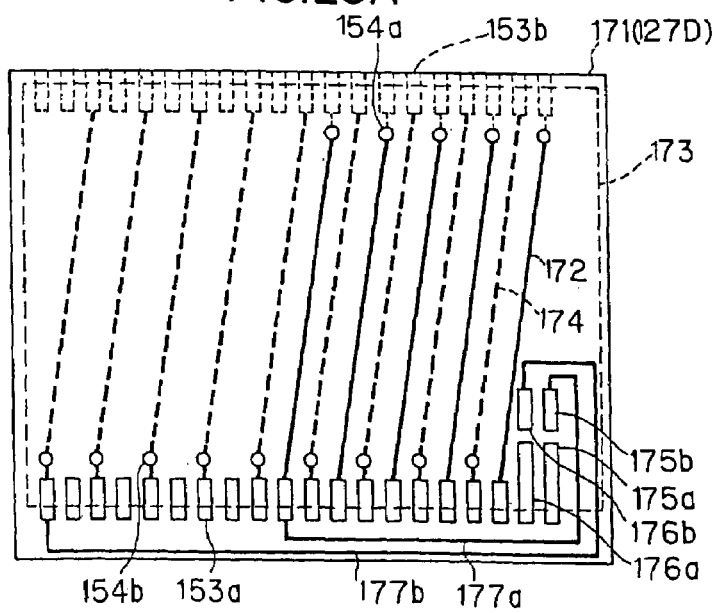
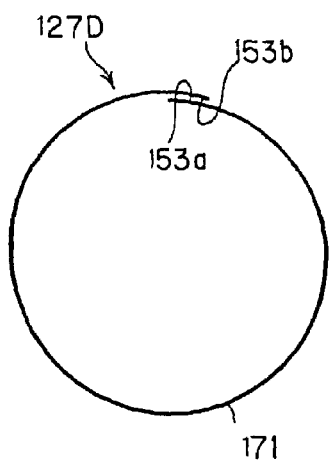
FIG.25B
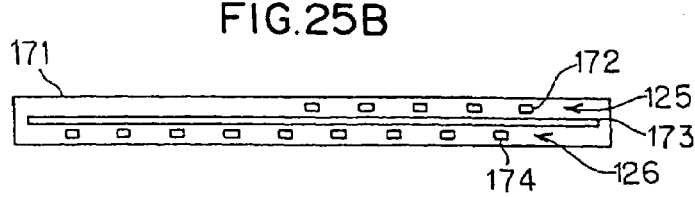

CAPSULE MEDICAL APPARATUS

This application claims benefit of Japanese Application No. 2003-366575 filed on Oct. 27, 2003, and No. 2003-368045 filed on Oct. 28, 2003, the contents of which are incorporated by this reference.

BACKGROUND OF THE INVENTION

1. Field of the Invention

The present invention relates to a capsule medical apparatus which is inserted into the living body, obtains living-body information, sends the obtained living-body information to the outside of the living body, and performs treatment.

2. Description of the Related Art

Recently, various capsule medical apparatuses which are capsule-shaped are proposed. Further, in order to reduce the size of the capsule medical apparatus, electric energy is externally supplied to the capsule medical apparatus.

For example, Japanese Unexamined Patent Application Publication No. 2001-224551 discloses, as a first related art, one capsule medical apparatus for accommodating a power receiving antenna formed onto a flexible substrate. The receiving antenna receives power which is sent from the outside of the body, and the power is used as a power source of the capsule medical apparatus.

Further, Japanese Unexamined Patent Application Publication No. 2003-210395 discloses, as a second related art, another capsule medical apparatus in which a circuit part is mounted on a thin-film curved substrate.

Furthermore, U.S. Patent Publication No. 2002-165592 discloses, as a third related art, an image pickup device for living body, in which a coil is arranged in a capsule apparatus, electromagnetic energy externally-supplied is converted into electric power, and the power is supplied to an image sensor arranged in the capsule apparatus.

SUMMARY OF THE INVENTION

According to the present invention, a capsule medical apparatus which generates power by radio using an AC magnetic field includes:

a capsule casing; and a thin-film substrate which is arranged in the capsule casing, wherein a wiring is formed on the thin-film substrate such that a spiral coil for receiving the AC magnetic field is constructed by cylindrically shaping the thin-film substrate.

Further, according to the present invention, in a capsule medical apparatus which generates power by radio using an AC magnetic field, a power receiving antenna and a sending antenna contain the same coil member.

BRIEF DESCRIPTION OF THE DRAWINGS

FIGS. 1A to 8B relate to a first embodiment of the present invention, FIG. 1A is a diagram showing the structure of a capsule medical apparatus system according to the first embodiment of the present invention;

FIG. 3 is a block diagram showing the internal structure of the extracorporeal unit;

FIG. 4 is a sectional view showing the structure of a capsule medical apparatus according to a first modification;

FIG. 6 is a diagram showing the basic structure of a flexible substrate according to a third modification;

FIG. 7 is a sectional view showing the structure of a capsule medical apparatus according to a fourth modification;

FIG. 8B is a diagram showing a flexible substrate according to a sixth modification;

FIGS. 9A to 13 relate to a second embodiment, FIG. 9A is a longitudinal sectional view showing the structure of a capsule medical apparatus according to the second embodiment of the present invention;

FIG. 10A is a detailed diagram showing the flexible substrate shown in FIG. 9B;

FIG. 10B is a sectional view with respect to a line connecting points D, E, E', and D' shown in FIG. 10A;

FIG. 12A is a side view showing a flexible substrate and a capacitor vicinity according to a second modification;

FIG. 12B is a rear view seen from the right in FIG. 12A;

FIG. 13 is a diagram showing a flexible substrate according to a third modification;

FIGS. 14A to 15 relate to a third embodiment of the present invention, FIG. 14A is a longitudinal sectional view showing the structure of a capsule medical apparatus according to the third embodiment of the present invention;

FIG. 14B is a perspective view showing the structure before molding integrally with an exterior member shown in FIG. 14A;

FIG. 15 is a diagram showing the structure of a power receiving coil which is formed on a flexible substrate according to the third modification;

FIGS. 16A to 20 relate to a fourth embodiment of the present invention; FIG. 16A is a diagram showing the structure of a capsule medical system according to the fourth embodiment of the present invention;

FIG. 17 is a block diagram showing the internal structure of the extracorporeal unit;

FIG. 19 is a block diagram showing the structure of an electric system in a capsule medical apparatus according to the fourth modification;

FIG. 20 is an explanatory diagram for an operation according to the fourth modification;

FIGS. 21A to 27B relate to a fifth embodiment of the present invention, FIG. 21A is a longitudinal sectional view showing the structure of a capsule medical apparatus according to the fifth embodiment of the present invention;

FIG. 23 is a block diagram showing the structure of an electric system in a capsule medical apparatus according to the first modification;

FIG. 24A is a diagram showing a state of developing a flexible substrate constituting a coil member shown in FIG. 23;

FIG. 24B is a diagram showing a cylindrical shape of the flexible substrate shown in FIG. 24A with its ends being connected;

FIG. 25A is a diagram showing the structure of a flexible substrate constituting a coil member according to the second modification;

FIG. 25B is a sectional view showing the structure in the thickness direction of the flexible substrate shown in FIG. 25A;

FIG. 25C is a diagram showing a cylindrical shape of the flexible substrate shown in FIG. 25A with its ends being connected;

FIG. 26 is a sectional view showing the structure of a coil member according to a third modification;

FIG. 27B is a diagram showing a state of connecting the flexible substrate shown in FIG. 27A with a cylindrical shape;

FIG. 28 is a block diagram showing the structure of an electric system in a capsule medical apparatus according to the sixth embodiment of the present invention; and FIG. 29 is an explanatory diagram of the operation according to the sixth embodiment.

DESCRIPTION OF THE PREFERRED EMBODIMENTS

Hereinbelow, embodiments of the present invention will be described later in accordance with the drawings.

First Embodiment

The first embodiment of the present invention will be described with reference to FIGS. 1A to 8B.

Figure 1A:
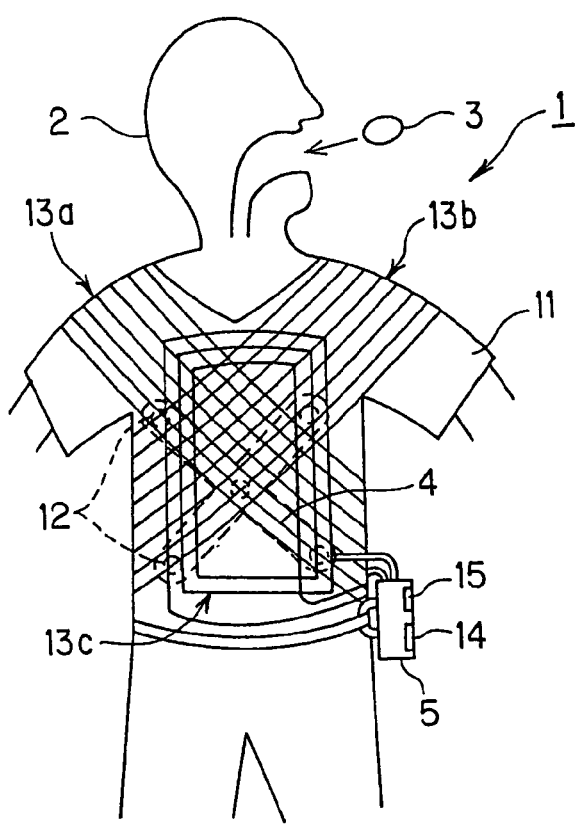

Referring to FIG. 1A, a capsule medical apparatus system 1 according to the first embodiment of the present invention comprises: a capsule medical apparatus 3 having a capsule endoscope function for sending, by radio, an image signal of an endoscope image obtained by optically picking-up an image of the line in the body cavity upon the passage through the line in the body cavity after being swollen from the mouth of a patient 2; an antenna unit 4 which is externally arranged to the patient 2; and an extracorporeal unit 5 (arranged to the outside of the patient 2) having a function for receiving a signal sent by the capsule medical apparatus 3 and storing the image.

The extracorporeal unit 5 includes a hard disk 18 (refer to FIG. 3) for storing image data. The hard disk 18 may be a compact flash (registered trademark) having a capacity of 1 GB.

Figure 1B:
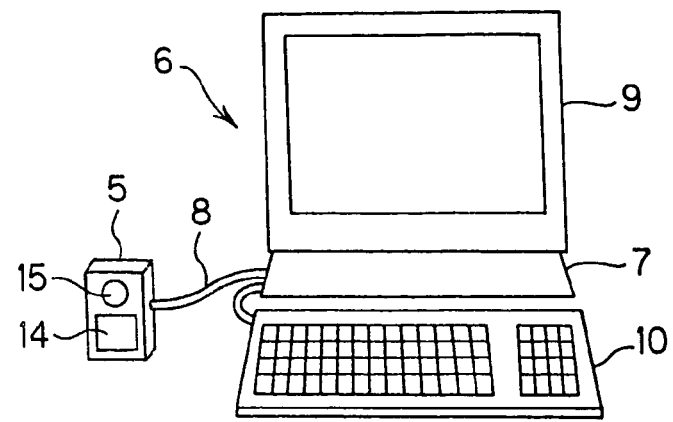
FIG. 1B is a diagram showing an extracorporeal unit and a personal computer.

During or after the examination, the image data stored in the extracorporeal unit 5 is sent to a display system 6 shown in FIG. 1B, thereby displaying the image.

Referring to FIG. 1B, the extracorporeal unit 5 is detachably connected to a personal computer (hereinafter, abbreviated to a PC) 7 forming the display system 6 via a communication cable such as a USB cable 8.

The PC 7 captures the image stored in the extracorporeal unit 5, and stores the captured image in an internal hard disk or displays the stored image on a display unit 9 after display processing. A keyboard 10 is connected as an operating board for inputting the data.

Referring to FIG. 1A, upon swallowing the capsule medical apparatus 3 and performing endoscope examination, the patient 2 dresses a shielding shirt 11 having a shielding function. The antenna unit 4 having a plurality of antennas 12 are arranged to the shielding shirt 11. Further, the antenna unit 4 is connected to the extracorporeal unit 5.

The extracorporeal unit 5 receives the signal sent from a sending coil in the antenna unit 4 thereby, which is picked-up by the capsule medical apparatus 3, and stores the pick-up image in the extracorporeal unit 5 connected to the antenna unit 4. The extracorporeal unit 5 is attached by a hook that is detachable to a belt of the patient 2.

According to the first embodiment, antenna coils (power sending coils) 13a and 13b generate AC magnetic fields in the shielded portion of the outer surface thereof and feed the power by radio or sends the power by radio. The antenna coils 13a and 13b are diagonally formed to the side from the shoulder, and an antenna coil 13c which is rectangularly wound and sends or feeds the power is formed, facing the front side and back side.

The antenna coils 13a to 13c are connected to the extracorporeal unit 5. The extracorporeal unit 5 is box-shaped and comprises a liquid crystal monitor 14 serving as a display device for displaying the image in front thereof and an operating unit 15 for control operation.

Figure 3:
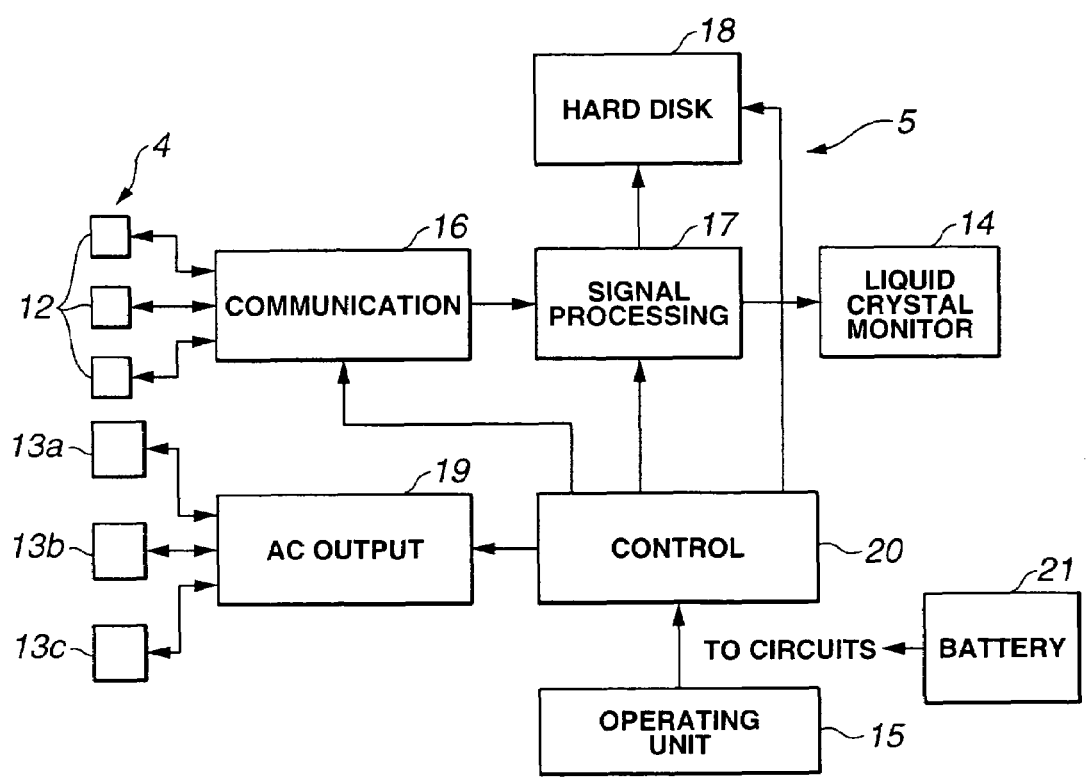

Referring to FIG. 3, the extracorporeal unit 5 comprises: the liquid crystal monitor 14; the operating unit 15; a communication circuit (radio communication circuit) 16 connected to the antenna 12; a signal processing circuit 17 for signal processing; the hard disk 18 for storing the image data after the signal processing; an AC output circuit 19 (comprising an oscillating circuit and a power amplifying circuit) for generating AC power outputted to the antenna coils 13a to 13c; a control circuit 20 for controlling the communication circuit 16; and a battery 21 serving as a power supply.

The antenna coils 13a to 13c generate the AC magnetic field by the AC power supplied from the AC output circuit 19. As will be described later, the AC magnetic field is 150 kHz or less at the low attenuation for the body, and the AC magnetic field is applied to the capsule medical apparatus 3 in the body.

The user operates the operating unit 15, thereby controlling the AC power supplied to the antenna coils 13a to 13c from the AC output circuit 19 via the control circuit 20. In the control operation of the AC power, the antenna coils 13a to 13c for supplying the AC power are selected, or sequentially switched and cyclically supplied. Alternatively, a period for sequentially the antennas 13a to 13c is selected.

Further, the user operates the operating unit 15 of the extracorporeal unit 5 and thus the control circuit 20 controls the operation for sending an operating signal to the capsule medical apparatus 3 via the communication circuit 16 and the antenna 12 and for controlling the image pick-up operation of the capsule medical apparatus 3. In this case, the capsule medical apparatus 3 receives the electric waves radiated from the antenna 12 by using a sending and receiving antenna 26 which will be described later.

Figure 2A:
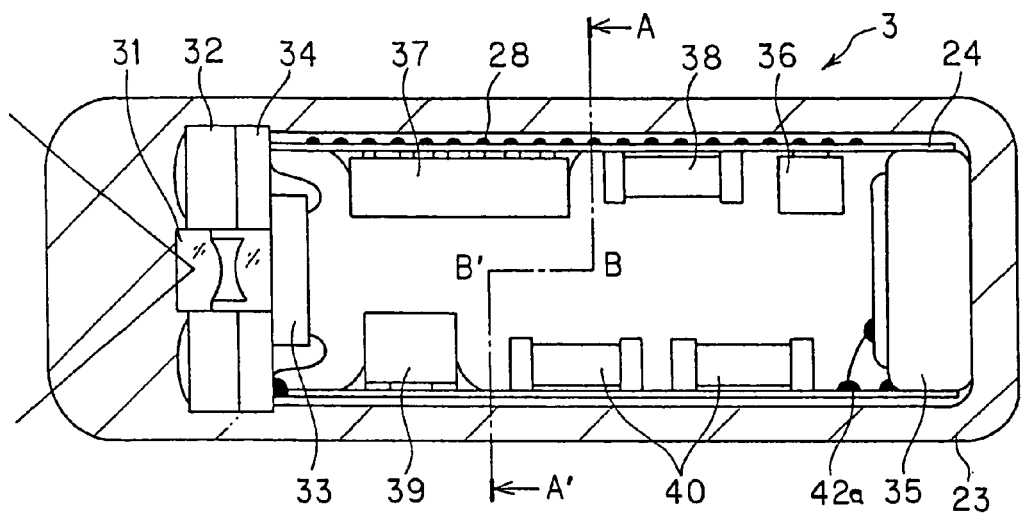
FIG. 2A is a longitudinal sectional view showing the internal structure of a capsule medical apparatus.
Figure 2B:
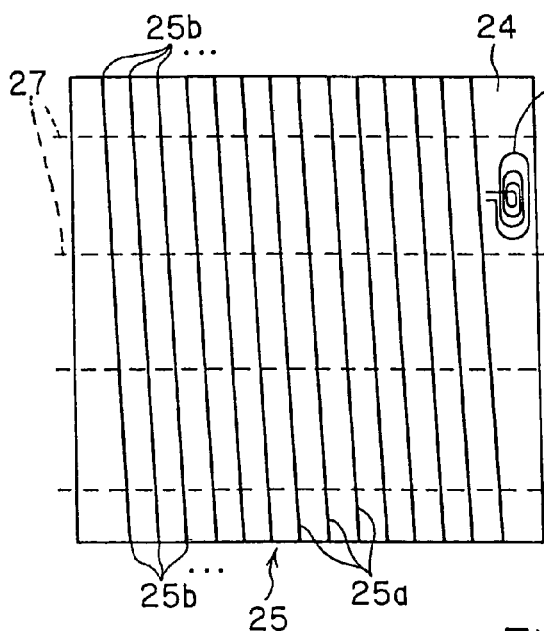
FIG. 2B is an outer development elevation for developing a flexible substrate.
Figure 2C:
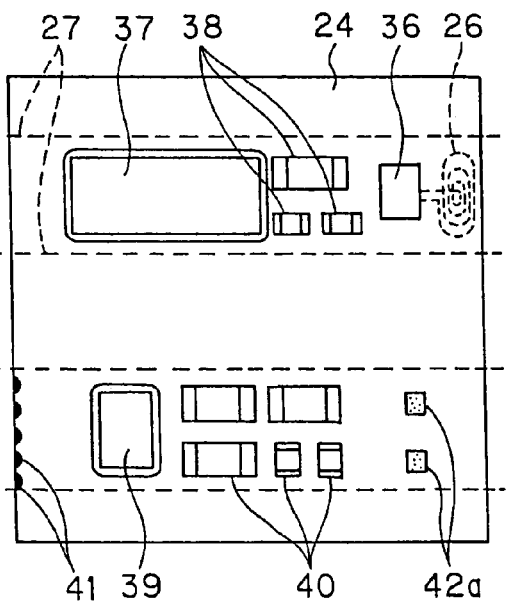
FIG. 2C is an inner development elevation for developing the flexible substrate.
Figure 2D:
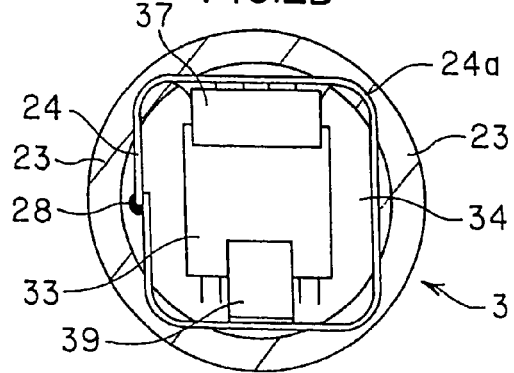
FIG. 2D is a sectional view of a line connecting points A, B, B', and A' shown in FIG. 2A.

Next, a description is given of the structure of the capsule medical apparatus 3 according to the first embodiment with reference to FIGS. 2A to 2D. FIG. 2A is a longitudinal sectional view showing the internal structure of the capsule medical apparatus. FIGS. 2B and 2C are outer and inner development elevations for developing a flexible substrate. FIG. 2D is a sectional view of a line connecting points A, B, B', and A' shown in FIG. 2A. Referring to FIG. 2A, a coil connecting unit 28 having two facing sides is shown in the cross section when a flexible substrate 24 like a thin film is cylindrically-shaped. Referring to FIG. 2D, the coil connecting unit 28 is in the side direction in which electric parts are not mounted.

Referring to FIG. 2A, the capsule medical apparatus 3 has a casing which is capsule-shaped and is sealed by an exterior member 23 that is integrally molded, containing resin such as Polysulfone. The exterior member 23 accommodates the flexible substrate 24 serving as a thin-film substrate that is formed into a substantially square-shaped-cylinder.

In the development elevations shown in FIGS. 2B and 2C, the flexible substrate 24 is specifically rectangular- or square-shaped. A large number of power receiving coil wirings 25a forming a power receiving coil 25 is formed onto an outer surface of the flexible substrate 24 (that is cylindrically-shaped) with a printing pattern like a parallel line, slightly inclined from the perpendicular direction of the axis of the cylindrical shape.

A sending and receiving antenna 26 (for sending and receiving the signal) is formed like a spider near one end of the flexible substrate 24. As mentioned above, the flexible substrate 24 having the power receiving coil wirings 25a are bent along a bending line 27 shown by a dotted line. Referring to FIG. 2D, the cross section is formed into a substantially square-shaped-cylinder.

In this case, ends 25b of the power receiving coil wirings 25a facing the two opposite sides of the flexible substrate 24 are overlapped in the case of bending as shown in FIG. 2D, and become the coil connecting unit 28 connected by soldering. Further, the power receiving coil 25 is formed by spirally winding the power receiving coil wirings 25a. The flexible substrate 24 is fixed like square- and cylindrical shape. Referring to FIG. 2D, the flexible substrate 24 has a thin portion 24a which is thin near the bending line 27 to be easily bent and processed.

Near one end of the flexible substrate 24 which is formed into a substantially square-shaped-cylinder, an objective lens system 31 for forming an optical image of the body cavity, an LED 32 for illumination, and a CCD 33 serving as a solid-state image pick-up device arranged to the image forming position of the objective lens system 31 are attached to a common LED substrate 34, thereby integrally forming illuminating means and image pick-up means. The circumference is covered with a transparent exterior member 23.

Further, near the other end of flexible substrate 24 which is formed into a substantially square-shaped-cylinder, a capacitor 35 having a large capacity, a so-called super-capacitor that can be charged is arranged. The circumference of the capacitor 35 is covered with the transparent exterior member exterior member 23.

Referring to FIG. 2A or 2C, electric parts are mounted on the inner surface of the flexible substrate 24.

Specifically, an integrated circuit (IC) mounted as a bare chip forming a sending and receiving circuit (radio circuit) 36 that is connected to the sending and receiving antenna 26 is mounted on the flexible substrate 24. Further, mounted on the flexible substrate 24 is an IC mounted as a bare chip which forms an (image pick-up and) control circuit 37 which systematically controls circuits and a function for performing signal processing of the image pick-up signal of the CCD 33. Furthermore, mounted on the flexible substrate 24 is an electric part 38 such as a chip resistor or a chip capacitor forming the sending and receiving circuit 36 and the control circuit 37.

An illuminating circuit for driving the LED 32 for illumination serving as the illuminating means is mounted on the LED substrate 34. However, it may be mounted on the flexible substrate 24.

Further, mounted on the inner surface of the flexible substrate 24, specifically, on the facing surface of the electric part such as the sending and receiving circuit 36, are a bare-chip IC forming a commutating circuit 39 for commutating the AC power generated in the power receiving coil 25 and for supplying the power to the capacitor 35 and electric parts 40 such as a chip resistor and a chip capacitor forming the commutating circuit 39.

An electrode pad 41 for connecting the CCD 33 is arranged to one end portion adjacent to the bare-chip IC forming the commutating circuit 39. An electrode pad 42a which is adjacent to the electric parts 40 and is connected to the capacitor 35 are arranged to the one end portion adjacent to the bare-chip IC forming the commutating circuit 39.

According to the first embodiment, the power receiving coil 25 is cylindrically-shaped with the outer diameter of the capsule medical apparatus 3, and a large number of wirings of spiral coils (or solenoid coils) forming the power receiving coil 25 are formed with the size approximate to the entire length in the longitudinal direction.

That is, the outer diameter of the power receiving coil 25 is effectively large, the size of the power receiving coil 25 in the longitudinal direction is formed with the same length as that of the exterior member 23, and a large number of coil wirings are formed. Further, the space is thinly cylindrically-shaped, thus accommodating the space in a small space. Therefore, the size of the capsule medical apparatus 3 is reduced.

In the case of supplying the electric energy generated by the AC magnetic field from the external-body antenna coils 13a to 13c, the AC magnetic field having the frequency of several tens 10 Hz to 150 kHz is applied without using a high-frequency band (e.g., 10 MHz or more) that is influenced from the attenuation of electromagnetic waves in the body organ. For the AC magnetic field, the power receiving coil 25 increases in the cross-sectional area and the number of coil wirings, thus increasing the number of fluxes passing through the power receiving coil 25. The AC power is efficiently generated.

With the above-mentioned structure, the AC magnetic field is applied from the externally-arranged extracorporeal unit 5, and thus the AC electromotive force is efficiently generated by the AC magnetic field crossing the power receiving coil 25 arranged to the capsule medical apparatus 3 inserted in the body of the patient 2.

In this case, the cross-sectional area of the power receiving coil 25 is formed with the same size as the outer diameter of the exterior member 23. Therefore, the AC electromotive force is efficiently generated. Further, since the number of coils is plural, high AC electromotive force is generated.

The AC electromotive force generated by the power receiving coil 25 is shaped by the commutating circuit 39 and then is converted into DC power. After that, the DC power is stored in the capacitor 35, and the electric system in the capsule medical apparatus 3 is operated by using the AC charges serving as a power supply.

That is, the DC power supplied from the capacitor 35 intermittently enables the LED 32 for illumination serving as the illuminating means to intermittently emit light for illumination. Under the illumination, the CCD 33 forming the image pick-up means picks-up the image. The image pick-up signal of the CCD 33 is subjected to the signal processing by the control circuit 37. Further, the signal is A/D converted, the image data is compressed, and the compressed data is sent to the sending and receiving circuit 36. The sending and receiving circuit 36 modulates the data by the high frequency, and radiates the signal by electric waves via the sending and receiving antenna 26.

The electric waves are received by the antenna 12, and are demodulated by the communication circuit 16. After that, the demodulated signal is sent to the signal processing circuit 17. The hard disk 18 stores the compressed image data. The signal processing circuit 17 decompresses the compressed image data and then is converted into the video signal. Further, the converted signal is sent to the liquid crystal monitor 14. Finally, the liquid crystal monitor 14 checks (monitors) the endoscope image picked-up by the CCD 33.

According to the first embodiment, in the case of supplying the power of the AC magnetic field sent from the external body, the power receiving coil 25 efficiently generates the AC power. Therefore, it is possible to certainly operate the illuminating means and the image pick-up means for obtaining the endoscope image, which are arranged to the capsule medical apparatus 3.

Further, according to the first embodiment, the power receiving coil 25 is formed onto the flexible substrate 24 serving as the thin-film substrate. Therefore, the accommodating space is small and the mounting space of another internal parts is sufficiently ensured. The capsule medical apparatus 3 (serving as the capsule medical apparatus) for realizing the reduction in size and weight is realized.

Figure 4:
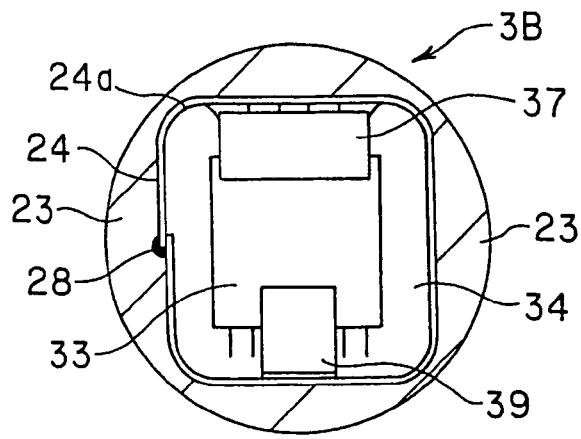

FIG. 4 shows the structure of a capsule medical apparatus 3B according to a first modification.

According to the first modification, FIG. 4 shows the cross-sectional structure of a line connecting points A, B, B', and A'. According to the first modification, the LED substrate 34 and the capacitor 35 are square-shaped, thus, the flexible substrate 24 is bent along the circumference of the square shape to be cylindrically-shaped approximately to the square, and the outer circumferential side is integrally molded by the exterior member 23.

Figure 5A:
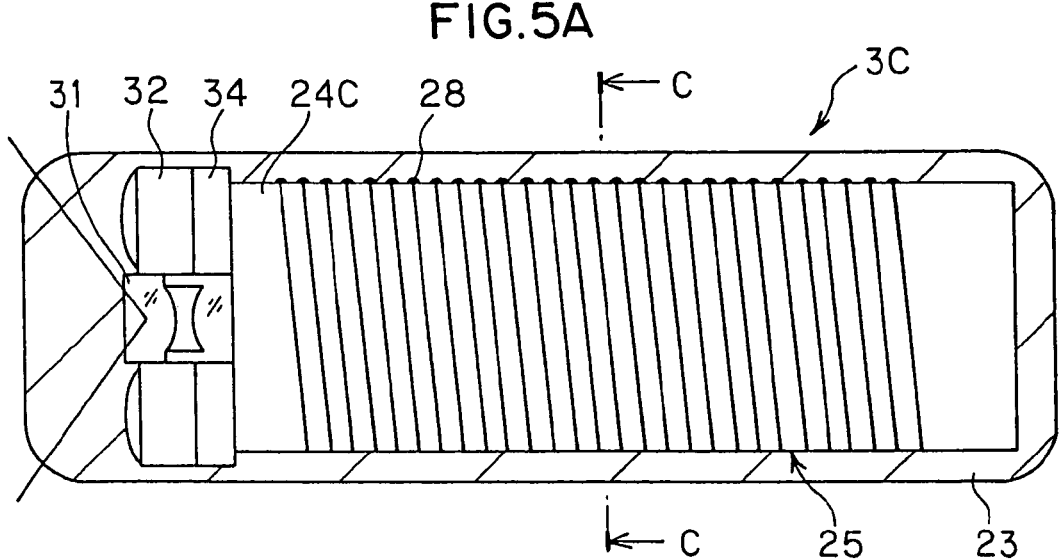
FIG. 5A is a sectional view showing the structure of a capsule medical apparatus according to a second modification.
Figure 5B:
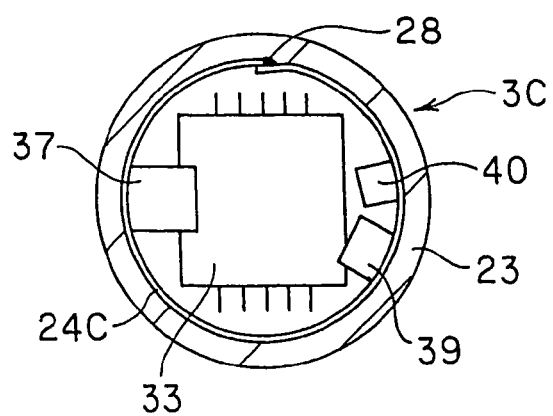
FIG. 5B is a sectional view of a line connecting points C shown in FIG. 5A.

FIGS. 5A and 5B show the structure of a capsule medical apparatus 3C according to a second modification. FIG. 5A shows a longitudinal sectional view. FIG. 5B shows a sectional view of a line connecting points C.

The capsule medical apparatus 3C according to the second modification uses a high-density multi-chip system on-film (high-density multi-chip SOF) technology and thus the above-mentioned control circuit 37 is mounted onto a flexible substrate 24C with a cylindrical-shape. This technology is described in detail in non-patent document 1 (Sharp Technical Journal 83 2002 pp. 16-18).

According to the high-density multi-chip SOF technology, the flexible substrate 24C is formed by arranging a Cu film onto a polyimide film that is thinly formed as much as possible, and the flexible substrate 24C is used. Thus, the bending operation and the like is further easy. Electric parts such as the control circuit 37 are curved-mounted onto the flexible substrate 24C.

The IC chip having the small-sized control circuit 37 or the like is used and thus the IC chip is easily mounted onto the cylindrical-shaped inner surface is easy.

With the above-mentioned structure, the cross-sectional area of the power receiving coil 25 is approximate to the outer diameter of the exterior member 23. Thus, the efficiency of power generation is improved.

According to the second modification, the flexible substrate 24C is cylindrically shaped and shown. However, in addition to a cylinder or square-shaped-cylinder, the flexible substrate 24C may be formed into a polygonally-shaped-cylinder such as an octagonally-shaped-cylinder. As the number of angles of the polygon is larger, advantageously, the area of the power receiving coil is increased.

Figure 6:
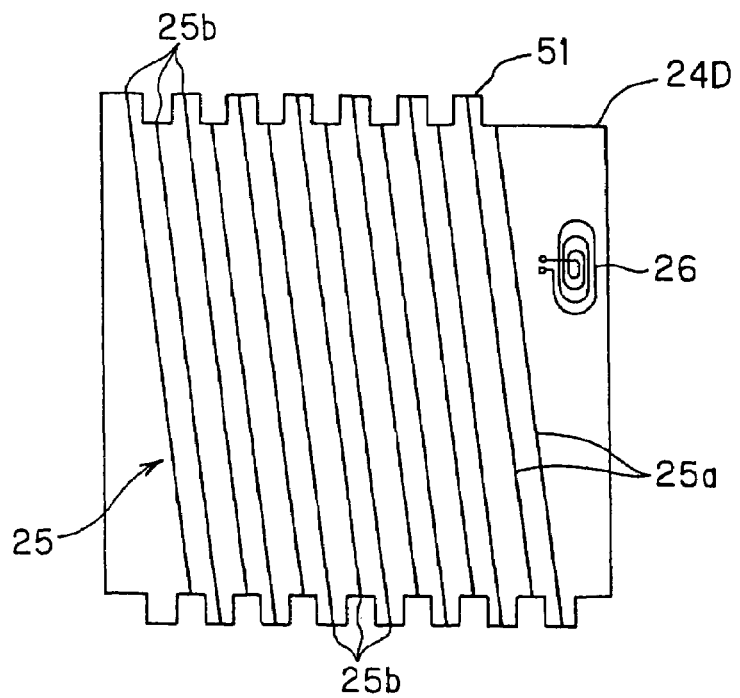

FIG. 6 shows a flexible substrate 24D according to a third modification. The flexible substrate 24D constitutes the power receiving coil 25 in the flexible substrate 24 as shown in FIG. 2B.

The shapes of the two sides of the flexible substrate 24D where the ends 25b of the coil wiring are exposed are formed by a rectangular wave portion 51 (the rectangular wave portion may be formed by a wave or sine-wave portion instead).

In the case of the straight line as shown in FIG. 2B, in an electric connection by soldering, for example, the area for soldering is not sufficient. The interval between the adjacent connecting portions is not reduced so as to prevent the short-circuited connection. According to the third modification, the electrically-connected area is alternately shifted and the soldering is easy without short-circuited connection. Further, the reduction in interval increases the number of coils and thus the electromotive force is increased.

Figure 7:
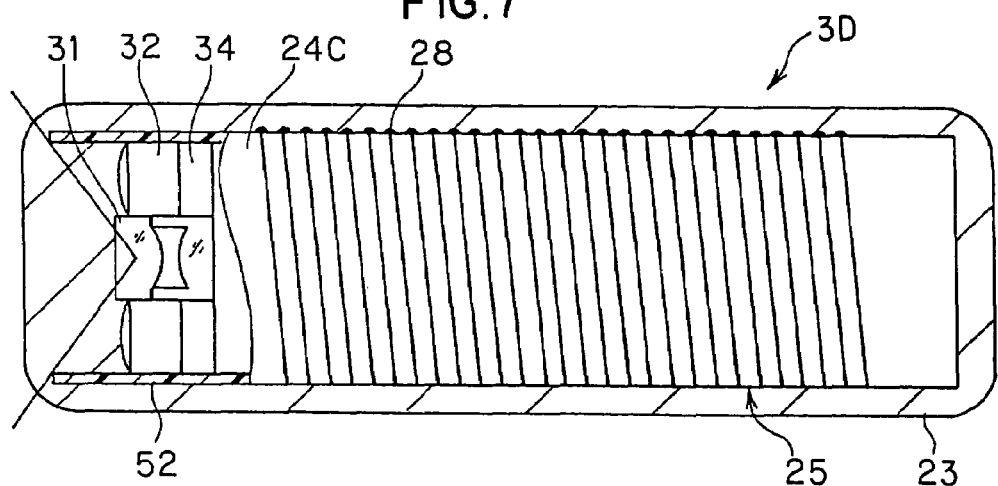

FIG. 7 shows the structure of a capsule medical apparatus 3D according to a fourth modification.

According to the fourth modification, one end portion at which the objective lens system 31 in the flexible substrate 24C shown in FIG. 5A is formed is extended, thereby arranging an extended portion 52 which is extended to a front of the objective lens system 31. The distal end of the extended portion 52 substantially matches on the point intersected with the boundary of the observing field-of-view of the objective lens system 31.

With the above-mentioned structure, the extended portion 52 of the flexible substrate 24C serving as the thin-film substrate is used as a hood of the objective lens system 31, and thus unnecessary light into the optical system is prevented. Therefore, according to the fourth medication, advantageously, the observing performance is improved.

Figure 8A:
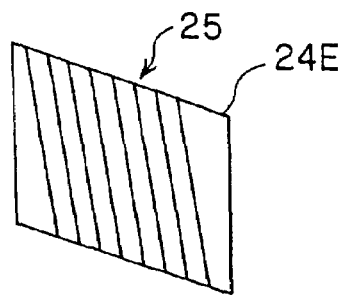
FIG. 8A is a diagram showing a flexible substrate according to a fifth modification.
Figure 8B:
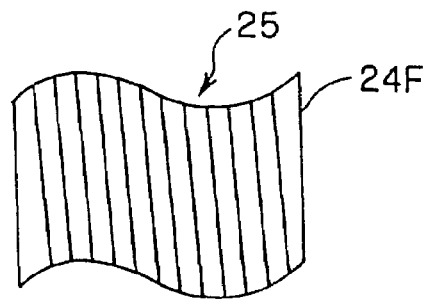

FIGS. 8A and 8B show flexible substrates 24E and 24F according to fifth and sixth modifications, respectively.

The thin-film substrate using the above-mentioned flexible substrate 24 or the like is approximately rectangular and, however, it is not limited to be rectangular. The thin-film substrate using the flexible substrate 24 may be the trapezoid-shaped flexible substrate 24E shown in FIG. 8A. Alternatively, the thin-film substrate using the flexible substrate 24 may be the wave-shaped flexible substrate 24F shown in FIG.

8B. That is, a cylindrically-shaped one will substitute. Further, the one which may improve the efficiency of power generation will substitute.

First, a description is given of the capacitor 35 serving as the charging means. The charging means is not limited to the capacitor and the charging means having a charging function may be a chargeable secondary battery. For example, it may be a NiMH (nickel-metal-hydride) battery or a lithium battery.

The capacitor 35 may use a super capacitor, an electric double-layer capacitor, or a ceramic capacitor. In this case, the ceramic capacitor is used and thus the liquid is not used. Consequently, the leakage of liquid in the capsule medical apparatus is prevented. Further, in the case of using the electric double-layer capacitor, the size is small and the electric capacitance is extremely increased. Thus, the stable power can be supplied.

Second Embodiment

Figure 9A:
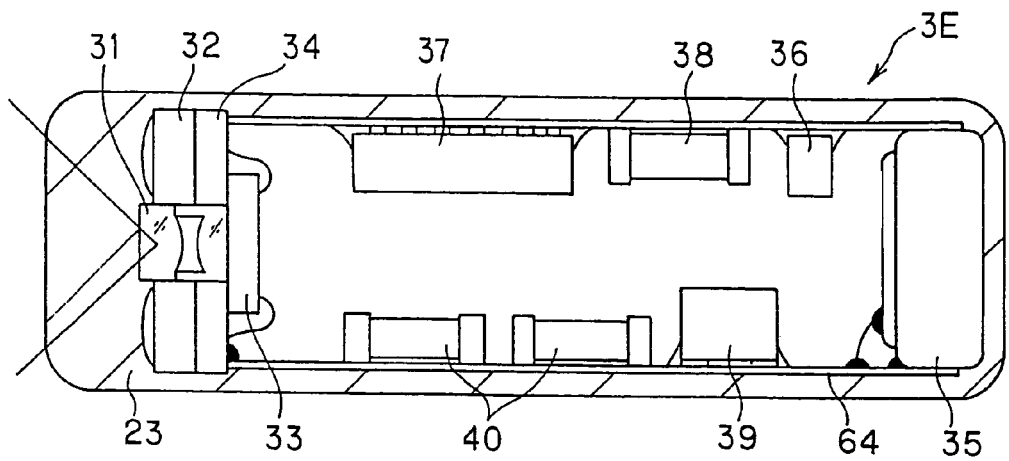

Next, a description is given of the second embodiment of the present invention with reference to FIGS. 9A to 10B. FIG. 9A shows a capsule medical apparatus 3E according to the second embodiment of the present invention.

The capsule medical apparatus 3E according to the second embodiment, serving as the thin-film substrate, uses a flexible substrate 64 comprising multi-layers, specifically, double-layers of a first-layer coil portion 61 and a second-layer coil portion 62, and a magnetic layer 63. The structure shown in FIG. 9A is the same as that of the capsule medical apparatus, excluding the use of the flexible substrate 64 in place of the flexible substrate 24 shown in FIG. 2A.

Figure 9B:
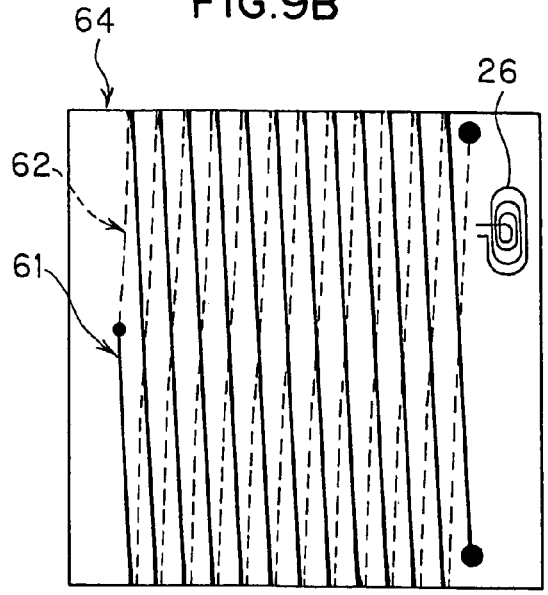
FIG. 9B is a diagram showing an outer surface in the case of developing the flexible substrate shown in FIG. 9A.

Referring to FIG. 9B, the first-layer coil portion 61 is formed onto the outer surface in the case of developing the flexible substrate 64 (before cylindrical assembling) according to the second embodiment, and the second-layer coil portion 62 is formed on the back side (the inside of the flexible substrate 64) thereof as shown by a dotted line.

Figure 9C:
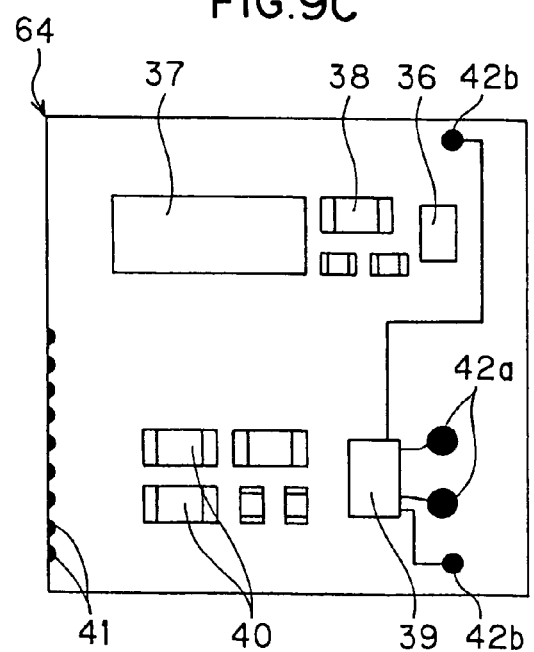
FIG. 9C is a diagram showing an innermost surface in the case of developing the flexible substrate shown in FIG. 9A.

Referring to FIG. 9C, a bare-chip IC forming the control circuit 37 is mounted onto the innermost surface of the flexible substrate 64. The bare-chip IC forming the commutating circuit 39 is connected to an electrode pad 42a connected to the capacitor 35 and an electrode pad 42b connected to the power receiving coil (formed by the first-layer coil portion 61 and the second-layer coil portion 62).

Figure 9D:
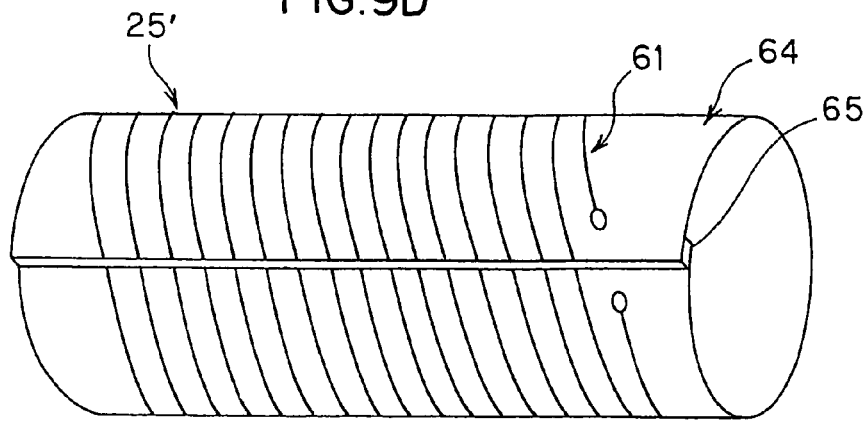
FIG. 9D is a diagram showing a cylindrical shape of the flexible substrate shown in FIG. 9B with its ends being connected.

FIG. 9D shows the appearance of the flexible substrate 64 shown in FIG. 9A that is cylindrically-shaped. Referring to FIG. 9D, an anisotropic conductive film (abbreviated to an ACF) 65 is inserted between the two different sides overlapped each other in the case of the flexible substrate 64 that is cylindrically-shaped. The ACF 65 electrically connects coil ends to form a power receiving coil 25'. The power receiving coil 25' comprises a power receiving coil using the first-layer coil portion 61 and a power receiving coil using the second-layer coil portion 62.

The ACF 65 is a film having the anisotropic conductivity and insulation. Specifically, the conductivity exhibits in the thickness direction, and the insulation exhibits in the surface direction perpendicular to the thickness direction. Therefore, inserting the ACF 65, the two ends on both the sides of the inserted portion of the power receiving coil 25 are electrically conducted (may be conducted by using the bump connection). Further, the insulation to the ends adjacent in the surface direction is ensured.

FIG. 10A shows in detail the flexible substrate 64 shown in FIG. 9A. FIG. 10B shows a sectional view of a line connecting points D, E, E', and D' in FIG. 10A.

Referring to FIGS. 10A and 10B, the flexible substrate 64 is formed by laminating the first-layer coil portion 61, the second-layer coil portion 62, and the magnetic layer 63. On the back side, a part mounting pattern layer 66 serving as double layers is formed. A ferromagnetic film 63a is formed to the magnetic layer 63 in a thin film like.

A large number of coil wirings are formed to the first-layer coil portion 61 and the second-layer coil portion 62 in parallel with each other in the direction perpendicular to the axis in the case in which the coils are cylindrically-shaped. In this case, the coil wirings are slightly inclined from the direction perpendicular to the axis in the first-layer coil portion 61 serving as the one coil portion. The coil wirings are slightly inclined to the opposite side from the direction perpendicular to the axis in the second-layer coil portion 62 serving as the other coil portion.

Referring to FIG. 9D, the flexible substrate 64 is cylindrically-shaped, and the coil ends are electrically connected by inserting the ACF 65 to the overlapped two sides. Referring to FIG. 10A, reference numerals a1 to a8 and b1 to b8 denote the connecting states of the coil ends in this case, respectively.

That is, a coil end ai (i=1 to 8) on the top side in FIG. 10A is connected to a coil end on the bottom side. A coil end bi on the top side is connected to a coil end bi on the bottom side. For the purpose of the connection, the ACF 65 is inserted such that the coil ends ai and bi on the top side respectively face the coil ends ai and bi on the bottom side.

By using a piece of the band-shaped ACF 65, the connection of the coil ends ai and bi is easy.

A terminal end of the first-layer coil portion 61 shown in FIG. 10A is connected to a start end of the second-layer coil portion 62 serving as the down layer by using a veer 67.

The start end of the first-layer coil portion 61 is communicated with the terminal end of the second-layer coil portion 62 by a veer 68 on the part mounting pattern layer 66 side. The veer 68 becomes an output terminal of the power receiving coil, and is connected to the commutating circuit 39.

According to the second embodiment, similarly to the first embodiment, the flexible substrate 64 serving as the thin-film substrate constitutes the power receiving coil 25', and the electric parts are mounted. Thus, a compact capsule medical apparatus is realized.

Further, according to the second embodiment, the coil wiring in which the power receiving coil 25' is arranged to the two layers so that the number of coils is doubled. Consequently, the AC electromotive force for the AC magnetic filed is doubled. That is, the power generating function is doubled for the AC magnetic field. As shown in the sectional view of FIG. 10B, the thin-film substrate has the magnetic layer 63 including a permalloy film. Therefore, the efficiency for focusing magnetic flux is improved and the efficiency of power generation is further improved. The magnetic layer 63 is not limited to the permalloy film and it may be any substance with a rate magnetic permeability at the high level, such as pure iron, super malloy, nickel, or silicon steel.

Instead that the magnetic member is arranged in the thin film, a rod (stick-shaped, cylindrical-shaped, polygonal-column) or a pipe containing the magnetic member may be arranged in a space in the cylindrical thin-film coil (which will be described later with reference to FIG. 14A).

Figure 11A:
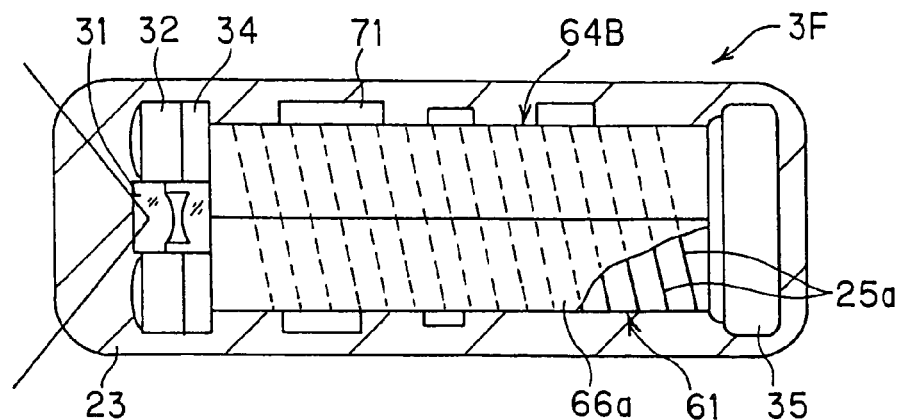
FIG. 11A is a longitudinal sectional view showing the structure of a capsule medical apparatus according to a first modification.
Figure 11B:
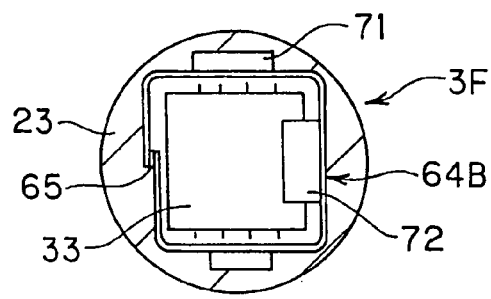
FIG. 11B is a lateral sectional view of FIG. 11A.

FIG. 11A shows the capsule medical apparatus 3F according to a first modification. In the capsule medical apparatus 3F, an electric part 71 is mounted not only on the inside of the cylindrical portion of the flexible substrate 64B but also on the outside. For example, when the cylindrical portion of the flexible substrate 64B is square-shaped, the outside has a space and therefore the electric part 71 is mounted on the space.

According to the first modification, one layer of the double-layer part mounting pattern layers 66 shown in FIG. 10B (which will be shown by reference numeral 66a in FIGS. 11A and 11C) is arranged to the outer layer of the first-layer coil portion 61.

In this case, the commutating circuit 39 or the sending and receiving antenna 26 which is preferably arranged to the outside is arranged, thereby improving the efficiency of sending and receiving of the signal.

Figure 11C:
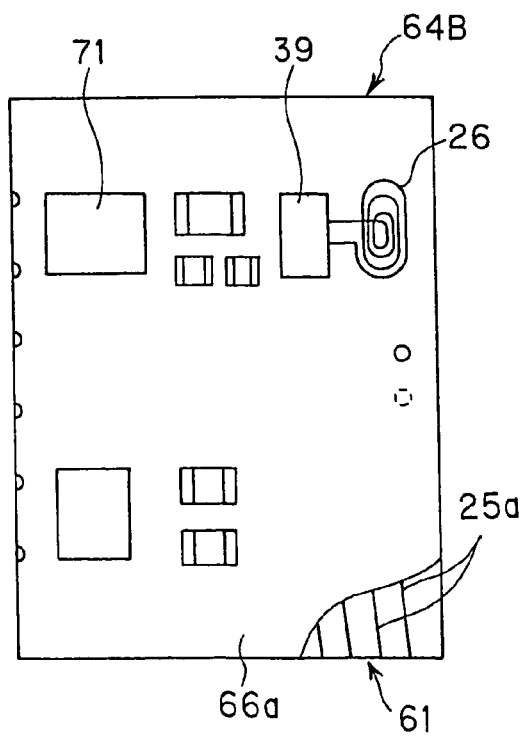
FIG. 11C is a diagram showing a state in which a part-mounting surface on the outer side shown in FIG. 11A is developed.
Figure 11D:
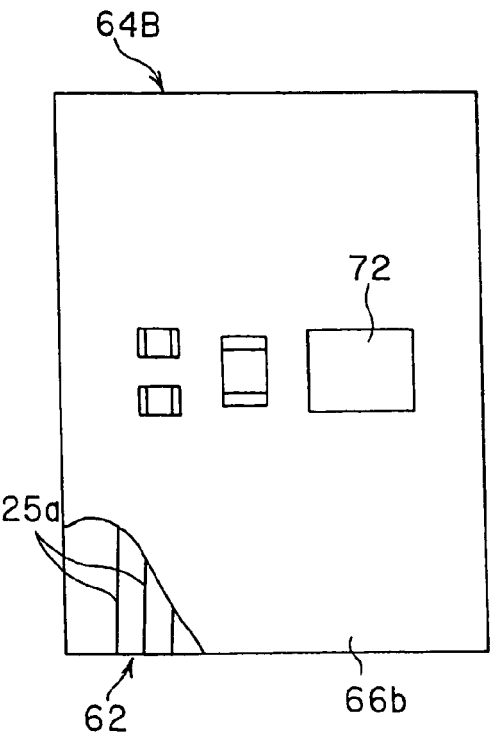
FIG. 11D is a diagram showing a state in which a part-mounting surface on the inner side shown in FIG. 11A is developed.

Referring to FIG. 11D, an electric part 72 is mounted on the other layer of the double-layer 66b part mounting pattern layers 66, which will be shown by reference numeral 66b in FIGS. 11A and 11C, on the innermost side. According to the first modification, the same advantages as those according to the second embodiment with reference to FIGS. 9A to 9D are obtained. FIGS. 12A and 12B show a connecting portion between the capacitor 35 and the flexible substrate 64 according to a second modification. FIG. 12A shows a side view. FIG. 12B shows a rear view seen from the right.

The flexible substrate 64C according to the second modification has an extended portion 64d which is formed by extending the end side connected to the capacitor 35 in the flexible substrate 64 shown in FIG. 9A, the extended portion 64d being bent along the outer shape of the capacitor 35 and is connected.

With the above-mentioned structure, the setting area is increased and the large amount of power is stably flowed. Advantageously, the stabilization of the power supply to the capsule medical apparatus is realized according to the second modification.

Figure 13:
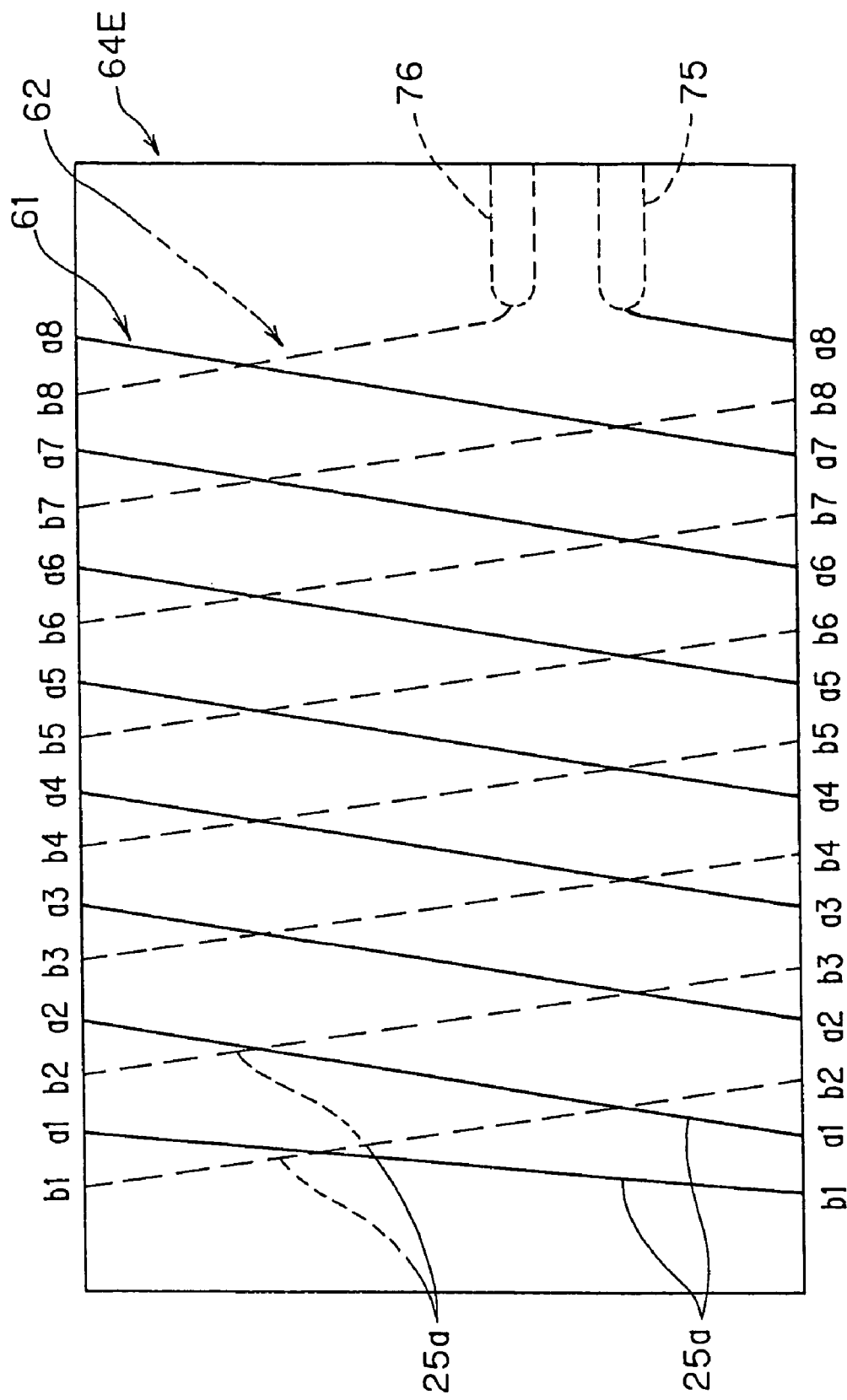

FIG. 13 shows a flexible substrate 64E according to a third modification. The end of the first-layer coil portion 61 is connected to the end of the second-layer coil portion 62 by veer connection on the flexible substrate 64 as shown in FIG. 10A or the like. However, according to the third modification, ends b1 of the two sides are connected.

On the flexible substrate 64E, the start end of the first-layer coil portion 61 serving as the output terminal of the power receiving coil and the terminal end of the second-layer coil portion 62 are respectively connected to patterns 75 and 76 having a wide width. The patterns 75 and 76 are exposed to the part mounting pattern layer 66, which are formed by notching the facing portions, and are easily connected to the commutating circuit.

According to the third modification, the wiring of the thin-film substrate is simplified.

Third Embodiment

Next, a description is given of the third embodiment of the present invention with reference to FIGS. 14A and 14B. FIG. 14A shows a capsule medical apparatus 3G according to the third embodiment of the present invention.

Referring to FIG. 14A, the capsule medical apparatus 3G according to the third embodiment uses a flexible substrate 81 which is cylindrically-shaped, e.g., square-shaped-cylinder having the axis in the direction perpendicular to the longitudinal direction of the capsule medical apparatus 3G (here, upward direction).

A coil wiring 82a is arranged along the outer circumferential surface of the cylindrical member, thereby forming a power receiving coil 82.

That is, the structure before integrally molding with the exterior member 23 is as shown in FIG. 14B. The power receiving coil 82 is formed along the outer circumferential surface of the cylindrical member.

Referring to FIG. 14A, the antenna 26, the sending and receiving circuit 36, the control circuit 37, and the like are mounted on the inside of the flexible substrate 81. A magnetic member 83 which is rod-shaped like an iron core is arranged to a free space of the flexible substrate 81. In order to prevent the generation of overflow of current, the thin films are laminated to be rod-shaped, or powders are pressured to be rod-shaped.

Referring to FIG. 14B, the flexible substrate 81 has an extended portion 84, and one end of the extended portion 84 is electrically connected to the LED substrate 34. According to the third embodiment, the thin-film substrate is cylindrically-shaped with the axis in the direction vertical to the longitudinal axis of the capsule medical apparatus 3G, and the power receiving coil 82 is formed by the thin-film substrate. The cross-sectional area of the power receiving coil 82 is formed with the maximum and thus the efficiency of power generation is expected.

Similarly to the first embodiment and the second embodiment, since the circuit parts are mounted on the thin-film substrate in the cylindrically-shaped power receiving coil 82, the compact capsule medical apparatus 3G is constructed. Further, since the iron core containing pure iron is arranged in the free space, the efficiency of power generation is improved.

Further, according to a first modification, referring to FIG. 15, a flexible substrate 81B has two cylindrical portions 85 and 86 which are perpendicular to the longitudinal direction of the capsule medical apparatus 3G (shown in FIG. 14A) and are perpendicular each other. A first power-receiving coil wiring 87a and a second power-receiving coil wiring 88a having power receiving coils 87 and 88 at the cylindrical portions 85 and 86 may be formed.

According to the first modification, the power receiving coils 87 and 88 are arranged to the thin-film substrate having the two cylindrical portions which are perpendicular each other. Therefore, if the direction of the capsule medical apparatus is changed, the power receiving coils 87 and 88 efficiently generate the power in the two different directions. In other words, the variation in efficiency of power generation due to the direction of magnetic field is suppressed.

According to a second modification, referring to FIG. 15, the flexible substrate 24 according to the first embodiment may be arranged in the cylindrical portion 85, in place of the cylindrical portion 86. In this case, the same advantages as those according to the first modification are obtained.

According to the first to third embodiments, the AC magnetic field is received externally from the living body by the spiral coils which are cylindrically formed and thus the AC power is efficiently generated. Further, since the spiral coils are formed by wiring arranged in the thin-film substrate, the mounting space is reduced, the incorporated parts are mounted compactly, and the capsule medical apparatus is reduced in size.

Further, according to the first to third embodiment, since the power receiving antenna and the sending antenna containing the same coil member, the capsule medical apparatus is reduced in size.

Fourth Embodiment

Next, the fourth embodiment of the present invention will be described with reference to FIGS. 16A to 20.

It is the object of the fourth embodiment to provide a compact capsule medical apparatus (specifically, a capsule endoscope) having a sending antenna suitable to the transmission of the large amount of data such as image data, serving as the living-body information, and a power receiving antenna suitable to power reception.

Figure 16A:
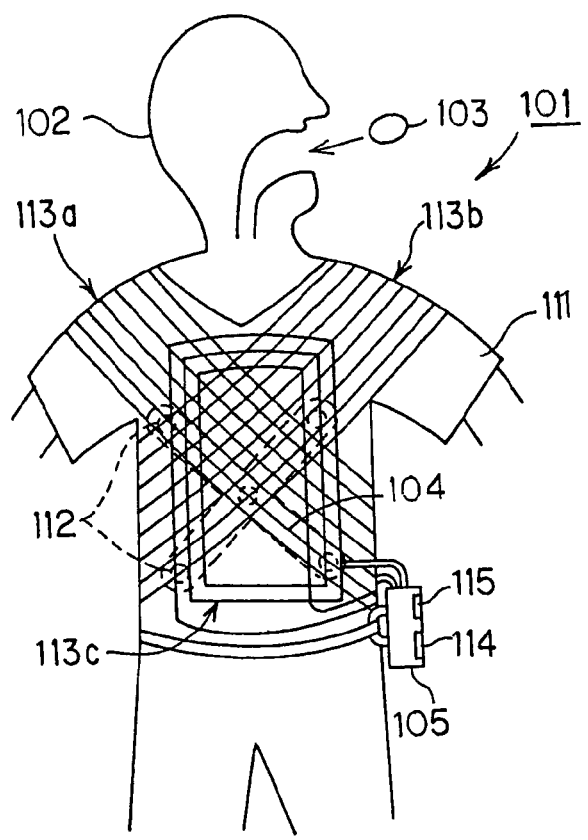

Referring to FIG. 16A, a capsule medical system 101 according to the fourth embodiment comprises a capsule medical apparatus 103 which is swallowed from the mouth of a patient 102 and has a function of a capsule endoscope for sending by radio the image information of the endoscope image that is obtained by optically picking-up an image of the lumen in the body cavity upon the passage through the lumen in the body cavity; and an extracorporeal unit 105 (externally-arranged to the patient 102) which has a function for receiving the signal sent by the capsule medical apparatus 103 by an antenna unit 104 externally-arranged to the patient 102 and for storing the image.

The extracorporeal unit 105 contains a hard disk 118 (refer to FIG. 17) for storing the image data. The hard disk 118 may be a compact flash (registered trademark) having a capacity of 1 GB.

Figure 16B:
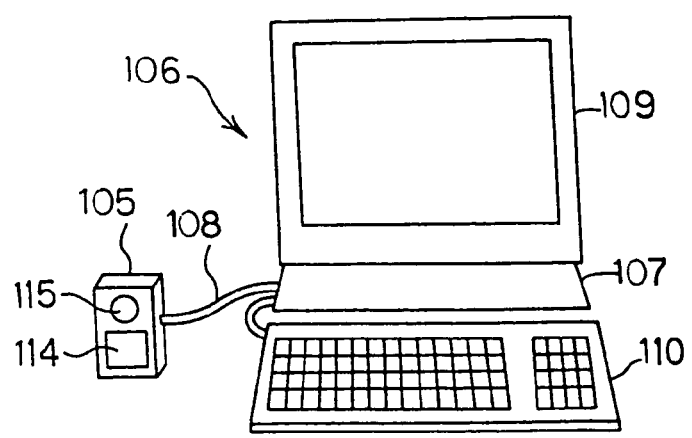
FIG. 16B is a diagram showing an extracorporeal unit and a personal computer.

By the connection to a display system 106 in FIG. 16B during the examination or after ending the examination, the image data stored in the extracorporeal unit 105 is displayed on the display system 106 as an image.

Referring to FIG. 16B, the extracorporeal unit 105 is freely detachably connected to a personal computer (hereinafter, abbreviated to a PC) 107 constituting the display system 106 via a communication cable such as a USB cable 108.

The PC 107 captures the image stored in the extracorporeal unit 105, performs the processing for storing the image in a hard disk and displaying the image, and displays the stored image on a display unit 109. A keyboard 110 serving as an operating board for inputting the data is connected to the PC 107.

Referring to FIG. 16A, upon swallowing the capsule medical apparatus 103 and performing endoscope examination, the patient 102 dresses a shielding shirt 111 having a shielding function.

The antenna unit 104 having a plurality of antennas 112 is arranged to the inside of the shielding shirt 111. Further, the antenna unit 104 is connected to the extracorporeal unit 105.

Figure 18A:
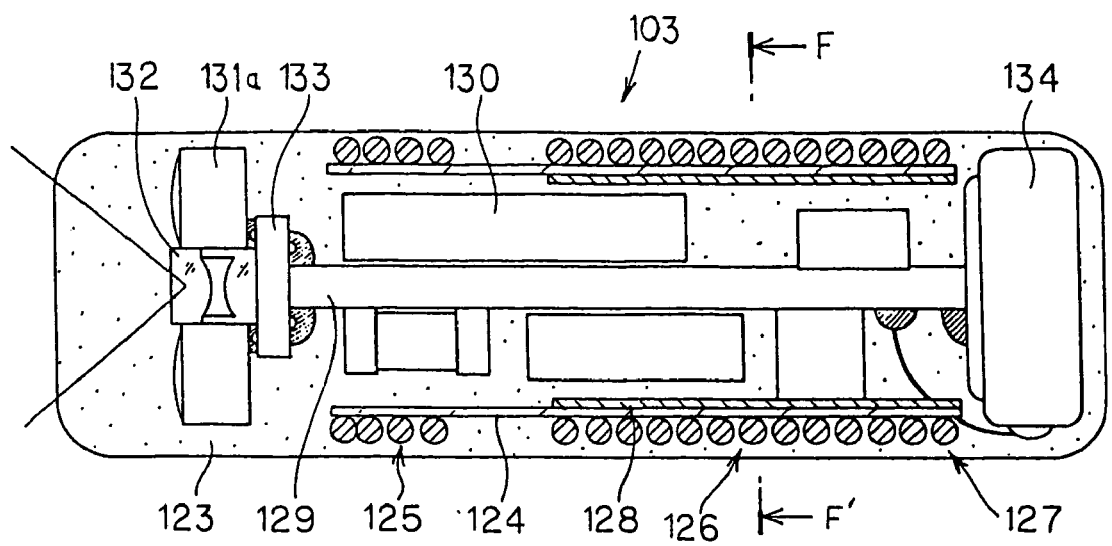
FIG. 18A is a longitudinal sectional view showing the structure of a capsule medical apparatus according to the fourth embodiment of the present invention.
Figure 18B:
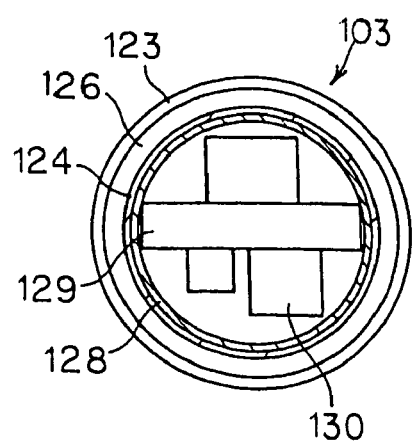
FIG. 18B is a sectional view of a line connecting points F and F' shown in FIG. 18A.
Figure 18C:
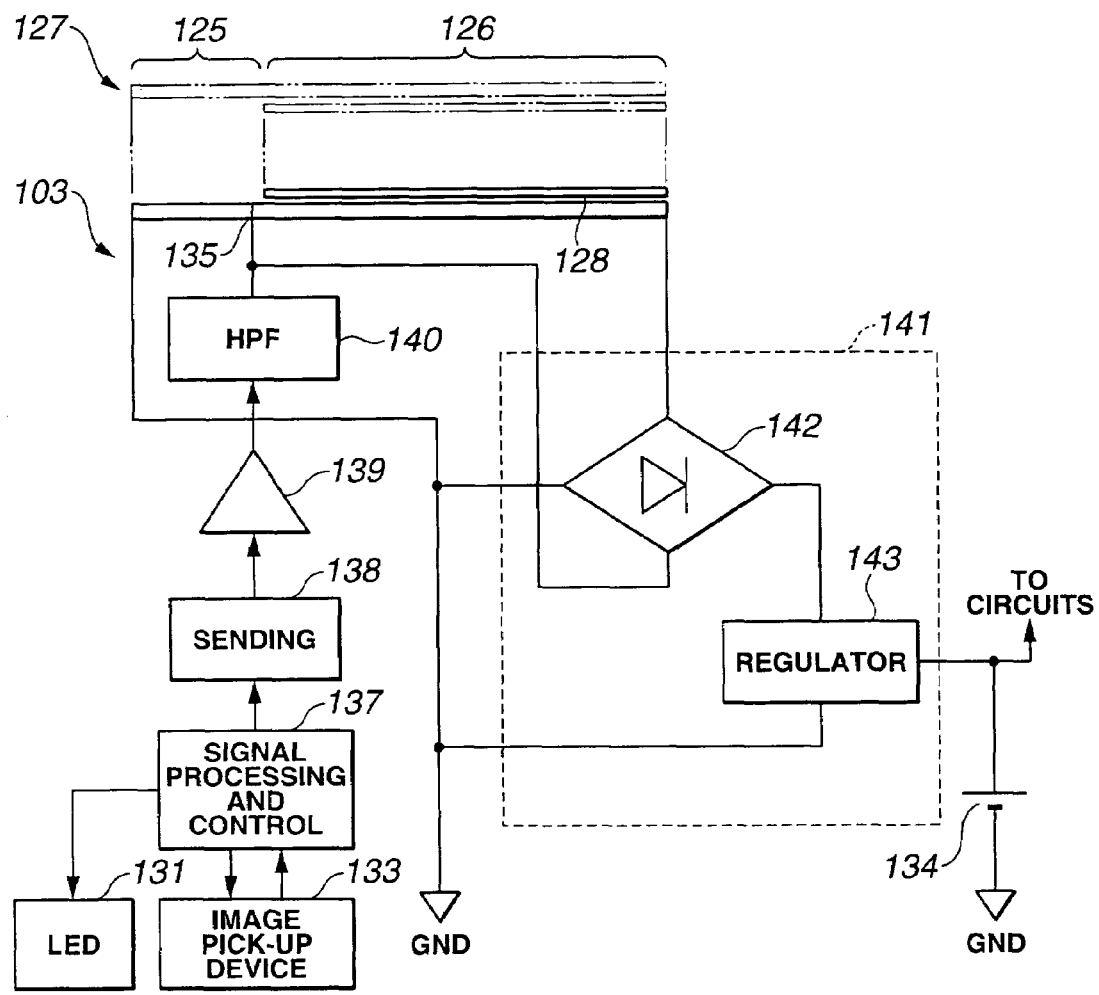
FIG. 18C is a diagram showing the structure of an electric system in the capsule medical apparatus.

The extracorporeal unit 105 receives by the antenna unit 104 connected thereto the signal of which image is obtained by picking-up the capsule medical apparatus 103 and further the signal is sent from a sending coil (refer to FIGS. 18A and 18C). The picked-up image is stored in the extracorporeal unit 105. The extracorporeal unit 105 is attached by a hook that is freely detachable to a belt of the patient 102.

According to the fourth embodiment, antenna coils (power sending coils) 113a and 113b generate AC magnetic fields in the inside of the shielded portion of the outer surface thereof and feed the power by radio or sends the power by radio. The antenna coils 113a and 113b are diagonally formed from the shoulder to the side of the patient with respect to his/her height, and antenna coils 113c which is rectangularly wound and sends or feeds the power are formed facing respectively the front side and back side.

The antenna coils 113a to 113c are connected to the extracorporeal unit 105.

The extracorporeal unit 105 is box-shaped and comprises in front thereof a liquid crystal monitor 114 serving as a display device for displaying the image and an operating unit 115 for control operation.

Figure 17:
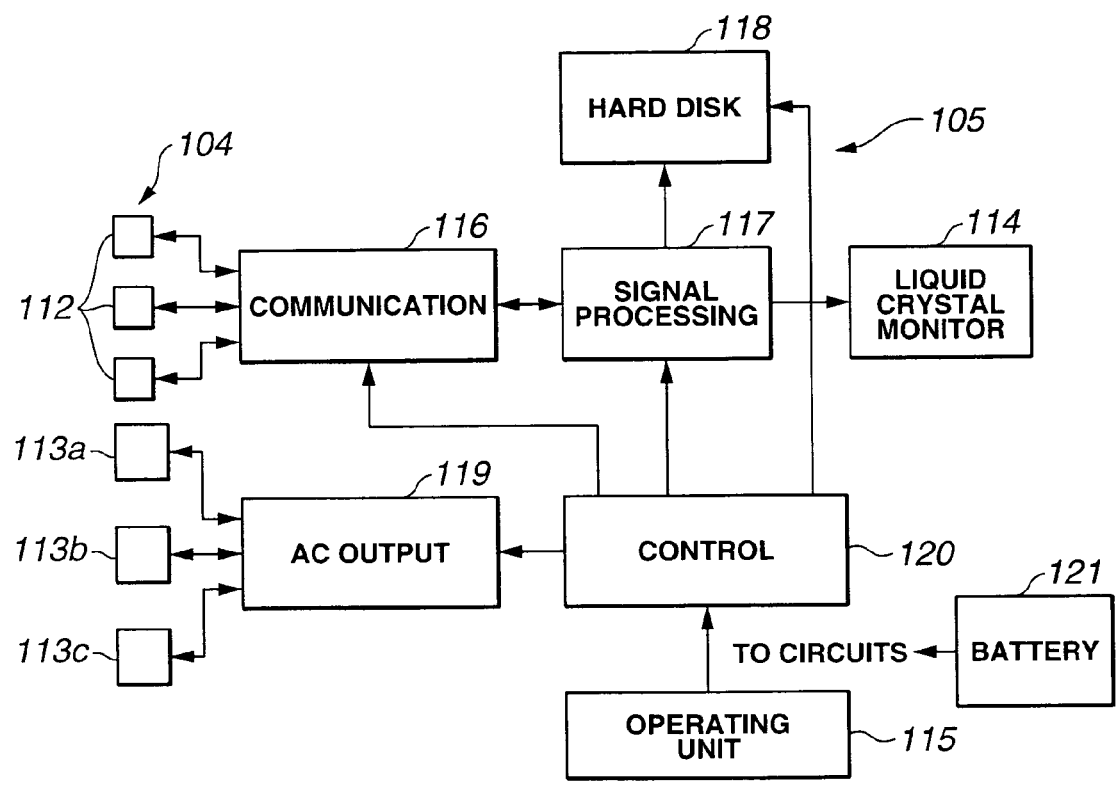

Referring to FIG. 17, the extracorporeal unit 105 comprises inside thereof: the liquid crystal monitor 114; the operating unit 115; a communication circuit (radio communication circuit) 116 connected to the antenna 112; a signal processing circuit 117 for signal processing; the hard disk 118 for storing the image data after the signal processing; an AC output circuit 119 for generating AC power outputted to the antenna coils 113a to 113c (comprising an oscillating circuit and a power amplifying circuit); a control circuit 120 for controlling the communication circuit 116; and a battery 121 serving as a power supply.

The antenna coils 113a to 113c generates the AC magnetic field by the AC power supplied from the AC output circuit 119. As will be described later, the AC magnetic field is 150 kHz or less at the low attenuation for the body, and the AC magnetic field is applied to the capsule medical apparatus 103 in the body.

Referring to FIG. 17, the antenna 112 is used only for the reception according to the fourth embodiment. However, according to the sixth embodiment, the antenna 112 is further used for the transmission. Therefore, according to the sixth embodiment, the communication circuit 116 is used not only for the reception but also for the transmission.

Next, a description is given of the capsule medical apparatus 103 according to the fourth embodiment with reference to FIGS. 18A to 18C. FIG. 18A is a longitudinal sectional view showing the internal structure of the capsule medical apparatus 103. FIG. 18B is a sectional view of a line connecting points F shown in FIG. 18A. FIG. 18C is a diagram showing the structure of an electric system in the capsule medical apparatus 103.

Referring to FIG. 18A, the capsule medical apparatus 103 is capsule-shaped by an integral molding resin 123. Embedded in the capsule medical apparatus 103 are a sending coil 125 for sending, by radio, the image information to the antenna 112 and a power receiving coil 126 for receiving the AC magnetic field by the antenna coils 113a to 113c and for generating the AC power.

That is, a coil member 127 having the sending coil 125 which is wound to the coil and is used for sending and the power receiving coil 126 serving as the power receiving antenna for externally receiving the AC power is arranged to the cylindrical outer-circumferential surface of a cylindrical-shaped coil core 124.

A magnetic cylindrical member 128 contains a ferromagnetic material such as Permalloy and has a function for focusing the magnetic field, that is, has a higher magnetic permeability. The magnetic cylindrical member 128 is arranged to the cylindrical inner circumferential surface of the coil core 124.

A rectangular-plate-shaped substrate 129 is arranged along the axis of the cylindrical coil core 124. An electric part 130 is mounted on the substrate 129. Referring to FIG. 18C, a circuit having a predetermined function is formed.

At one end of the flexible substrate 129, a disc-shaped LED substrate 131a on which an LED 131 for illumination (refer to FIG. 18C) is mounted is arranged. An objective lens system 132 for forming the optical image is attached to a through-hole portion arranged in the center of the LED 131. Further, an image pick-up device 133 is arranged at the image forming position of the objective lens system 132, thus illuminating means and image pick-up means are integrally formed.

The front surface of the image pick-up device 133 is flip-chip-mounted on the rear surface of the LED substrate 131a. The image pick-up device 133 has an electrode pad on the rear surface thereof. The electrode pad is soldered to a substrate 129, thereby electrically connecting the image pick-up device 133 to the substrate 129.

Further, at the other end of the substrate 129, a disc-shaped capacitor 134 with a large capacity having a function of charging means is arranged, and is electrically connected to the substrate 129.

The capsule medical apparatus 103 includes the coil member 127, the substrate 129 on which the electric part 130 is mounted therein, the LED substrate 131a arranged at both ends of the substrate 129, and the capacitor 134, the capsule medical apparatus 103 having an exterior member of the capsule-shaped outer form formed by pouring the integral molding resin 123 by using a mold having a capsule-shaped hollow portion (not shown).

According to the fourth embodiment, in the coil member 127, the coil is wound from one end side to near the other end over the center on the cylindrical outer circumferential surface of the common coil core 124, thereby forming the power receiving coil 126. Further, at a small interval, the same coil is wound by the small number of wirings to the adjacent other end, thereby forming the sending coil 125. One end of the power receiving coil 126 and one end of the sending coil 125 become a common terminal 135 or an intermediate electrode (FIG. 18C).

According to the fourth embodiment, the sending coil 125 is formed by using the small number of wirings wound to the outer circumferential surface of the coil core 124 and the power receiving coil 126 is formed by using the sufficiently large number of wirings. The sending coil 125 formed by the small number of wirings corresponds to a high-frequency band (several tens MHz or more) suitable to the data transfer. The power receiving coil 126 has the large number of wirings (and large cross-sectional area) so as to efficiently generate the AC power for the AC magnetic field having a low frequency.

According to the fourth embodiment, both functions are formed by the single coil member 127, thereby reducing the size of the capsule medical apparatus 103.

The magnetic cylindrical member 128 arranged in the coil core 124 is arranged only at the inner portion of the power receiving coil 126, and does not influence on the sending coil 125 which is formed apart a little from the power receiving coil 126.

FIG. 18C shows the structure of an electric system of the capsule medical apparatus 103.

The LED 131 and the image pick-up device 133 are connected to a signal processing and control circuit 137 which drives the LED 131 and the image pick-up device 133 and performs signal processing of an output signal of the image pick-up device 133. The signal processing and control circuit 137 A/D converts the image pick-up signal, converts the signal into the compressed image data, and sends the converted data to a sending circuit 138. The sending circuit 138 modulates the image data with a high frequency, and amplifies the modulated data by an amplifier 139. After that, the amplified signal passes through a high-pass filter (hereinafter, abbreviated to an HPF) 140, and is sent to the sending coil 125. The sending coil 125 radiates the image data as the electric waves with a high frequency.

Both ends of the power receiving coil 126 are connected to a diode bridge 142 forming a power feed circuit (charging circuit) 141. A commutative output commutated by the diode bridge 142 is inputted to a regulator circuit 143. The regulator circuit 143 smoothes and increases the voltage to convert the voltage to a predetermined DC voltage and then the converted voltage is supplied to the capacitor 134.

The AC power generated in the power receiving coil 126 is converted into DC power via the power feed circuit 141 and then is stored in the capacitor 134.

The sending coil 125 and the power receiving coil 126 are in common at the terminal 135. Therefore, the HPF 140 is inserted to prevent the invasion of the signal having a frequency so as to prevent that the unprofitable influence is caused by the signal, by serving as the noises and having the frequency of the AC magnetic field received by the power receiving coil 126 and supplied to the power feed circuit 141 to the sending circuit 138, when sending the sending signal amplified via the amplifier 139 from the sending circuit 138 to the sending coil 125 via the terminal 135. The HPF 140 has a function for preventing the input, to the sending circuit 138, of the signal having a low frequency (excessively lower compared with the sending signal, specifically, 1/100 or less) supplied to the power feed circuit 141.

The DC power charged in the capacitor 134 is supplied for the operation to the circuits such as the signal processing and control circuit 137 comprising the electric part 130 mounted on the substrate 129. The operation with the above-mentioned structure will be described according to the fourth embodiment.

Referring to FIG. 16A, the patient 102 dresses the shielding shirt 111 to attach the extracorporeal unit 105 and then swallows the capsule medical apparatus 103 from the mouth. In this case, the AC magnetic field is applied to the antenna coils 113a to 113c in advance, the power receiving coil 126 of the capsule medical apparatus 103 receives the power, and the power feed circuit 141 converts the AC power into the DC power and charges the capacitor 134. The circuits in the capsule medical apparatus 103 are operated by the DC power stored in the capacitor 134, and the normal operation of the circuits in the capsule medical apparatus 103 is checked. Then, the patient 102 swallows the capsule medical apparatus 103.

The signal processing and control circuit 137 in the capsule medical apparatus 103 controls the driving operation so as to intermittently emit light of the LED 131 serving as the illuminating means, and applies the driving signal to the image pick-up device 133. The image pick-up device 133 picks-up the image of the portion in the body cavity illuminated by the LED 131, and outputs, as an image pick-up signal, the signal charges which are photoelectrically converted by applying the driving signal.

The signal processing and control circuit 137 converts the signal into the image data, and compresses the image data. Then, the compressed image data is sent to the sending circuit 138. The sending circuit 138 modulates the data by a frequency of several tens MHz or more, and the amplifier 139 amplifies the modulated signal. After that, the amplified signal is supplied to the sending coil 125 via the HPF 140 through which the frequency of the several tens MHz or more passes, and is externally radiated as electric waves from the sending coil 125.

The electric waves are received by the antenna 112, and are demodulated by the communication circuit 116. After that, the demodulated signal is sent to the signal processing circuit 117. The compressed image data is stored in the hard disk 118 and is decompressed. Further, the decompressed signal is converted into the video signal, and is outputted to the liquid crystal monitor 114. The display screen of the liquid crystal monitor 114 displays the image picked-up by the image pick-up device 133.

By cyclically applying the AC magnetic field of the frequency of 150 kHz or less via the antenna coils 113a to 113c for a predetermined period from the extracorporeal unit 105, the AC electromotive force is induced in the power receiving coil 126 arranged in the capsule medical apparatus 103. The AC electromotive force is commutated by the diode bridge 142 and is converted into the DC power. Further, the regulator circuit 143 increases the voltage and stores the power in the capacitor 134.

According to the fourth embodiment, the AC magnetic field is externally applied by the low frequency. Thus, the AC magnetic field is applied to the capsule medical apparatus 103 in the body without attenuation. Since the AC power is efficiently fed from the outside, the capsule medical apparatus 103 can work on the operation of sending the living-body information in the body for a long time.

That is, in the case that only the battery included in the capsule medical apparatus 103 works, when the capsule medical apparatus 103 is operated for a long time, the electric energy of the battery is consumed and the sending of the living-body information stops on the way. However, according to the fourth embodiment, since the power is efficiently fed from the outside, the capsule medical apparatus 103 is operated for a long time.

As mentioned above, according to the fourth embodiment, the sending coil 125 and the power receiving coil 126 are formed in the single coil member 127. Further, the power receiving coil 126 has the same size as the outer diameter of the capsule medical apparatus 103 and is formed long and cylindrically-shaped so as to wind the large number of coils along the longitudinal direction of the capsule medical apparatus 103. Thus, the AC electromotive force induced by the power receiving coil 126 is increased.

That is, according to the fourth embodiment, the AC electromotive force is efficiently generated. In this case, in the power receiving coil 126, the magnetic cylindrical member 128 having the large magnetic permeability and the small loss is arranged within the frequency band of the AC magnetic field supplied from the antenna coils 113a to 113c. Thus, the AC electromotive force is efficiently generated.

According to the fourth embodiment, the antenna is suitable to send the signal having the high frequency with the small number of coils of the sending coil 125 and the high rate for sending the large amount of information of the image data (excessively higher than the frequency of the power receiving coil 126 having the sensitivity to the frequency of the AC magnetic field through the antenna coils 113a to 113c and to the AC magnetic field of the frequency).

The sending coil 125 and the power receiving coil 126 having the different frequency bands are formed into the single coil member 127. Thus, the capsule medical apparatus 103 is compact. This situation is complementarily described as follows.

The high frequency is advantageous for the increase in transfer rate to send, by radio, the data in the case of the large amount of information such as the image data. However, the high frequency is used for the power supply and then the attenuation is high in the living body. Consequently, the power is not efficiently sent.

Assume that the individual antennas are arranged for one frequency used for the power supply and for another frequency used for the data communication. Then, the space for the capsule medical apparatus is necessary and this is not preferable for the compact structure.

On the contrary, with the structure according to the fourth embodiment, the compact capsule medical apparatus 103 has the proper function with the saved space.

In the power supply using the electromagnetic induction, preferably, the magnetic material is arranged in the antenna (coil) for receiving the power. However, the communication antenna more efficiently radiates (receives) the electromagnetic waves if there is no magnetic material. This is considered according to the fourth embodiment.

Figure 19:
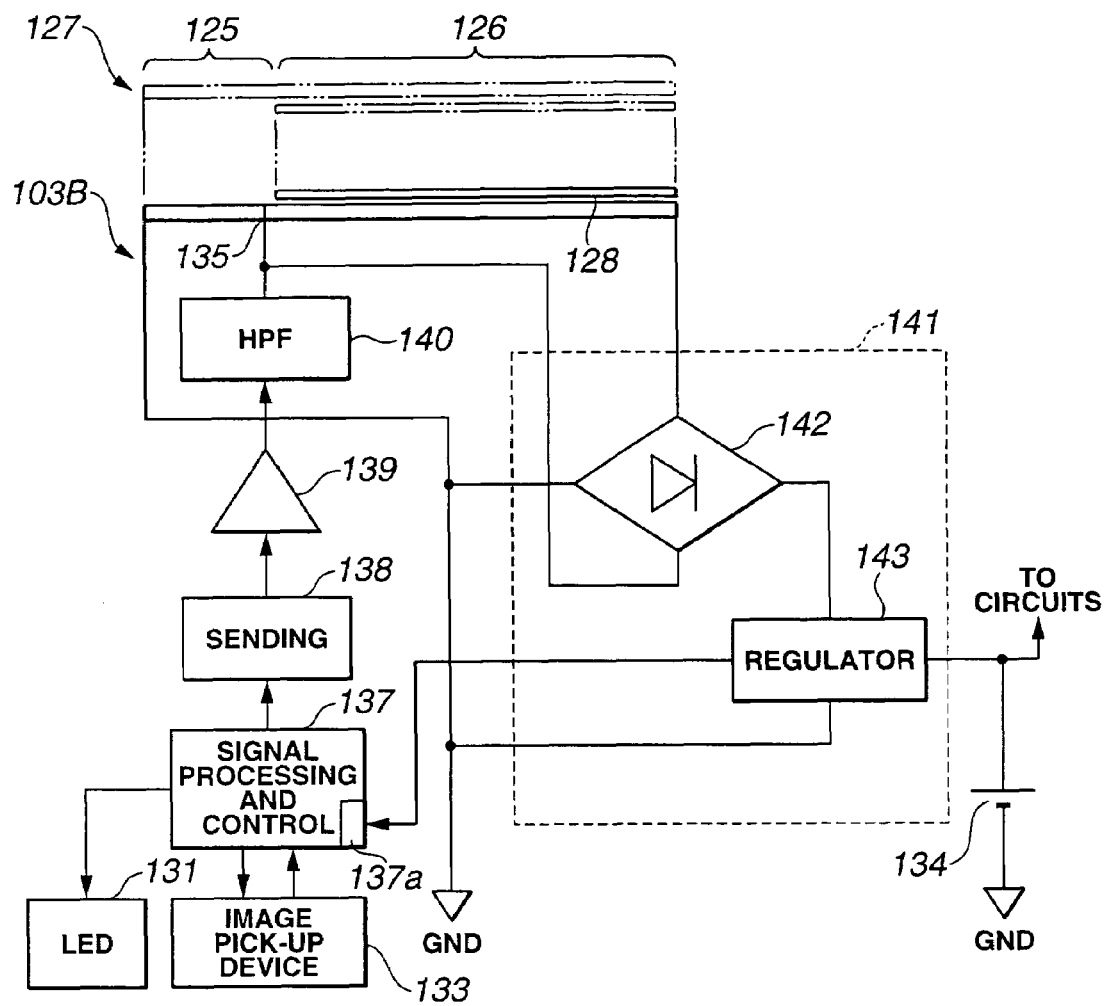

FIG. 19 shows the structure of an electric system of a capsule medical apparatus 103B according to a modification. With structure shown in FIG. 18C, the DC voltage inputted to the regulator circuit 143 is detected by a voltage monitoring unit 137a arranged to the signal processing and control circuit 137 according to a modification.

The signal processing and control circuit 137, by monitoring the DC voltage inputted to the regulator circuit 143 by using the voltage monitoring unit 137a, controls the sending circuit 138 so as to stop the sending of the signal when the power to the regulator circuit 143 is being fed by the power receiving coil 126, and so as to send the signal when the power feed operation is stopped.

Figure 20:
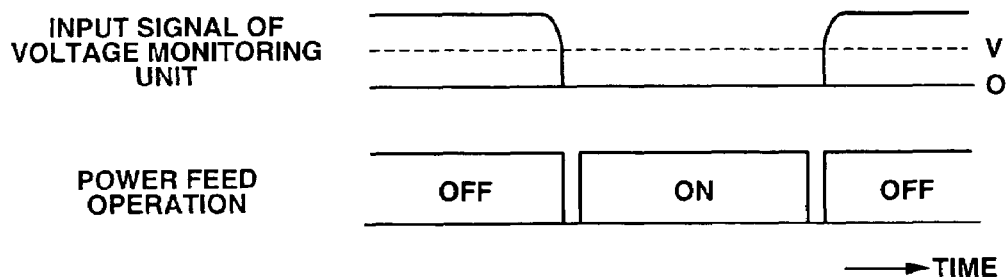

Referring to FIG. 20, the voltage monitoring unit 137a compares the level of the signal inputted to the voltage monitoring unit 137a with a predetermined voltage V, and sends a comparison result to, e.g., a CPU in the signal processing and control circuit 137. When detecting the input signal of the voltage V or more, the CPU stops (off) the sending operation of the sending circuit 138. When the input signal of the voltage V or more is not detected, the CPU switches on the sending operation of the sending circuit 138 or permits it.

As mentioned above, the time for sending the image data by the sending circuit 138 is different from the time for feeding (receiving) the power by the AC magnetic field.

According to the modification, upon sending the power, the above-mentioned control operation stops the generation of the AC magnetic field which causes the noises for the signal. Therefore, the capsule medical apparatus 103B can send the image data with the high quality. In addition, the capsule medical apparatus 103B has the same advantages as those capsule medical apparatus 103 shown in FIGS. 18A to 18C.

Fifth Embodiment

Next, the fifth embodiment of the present invention will be described with reference to FIGS. 21A to 22B. According to the fourth embodiment, the coil member 127 having the sending coil 125 and the power receiving coil 126 is formed by winding the coils about the coil core 124. However, according to the fifth embodiment, a coil member 127B having the sending coil 125 and the power receiving coil 126 is formed by using a flexible substrate 151.

Figure 21A:
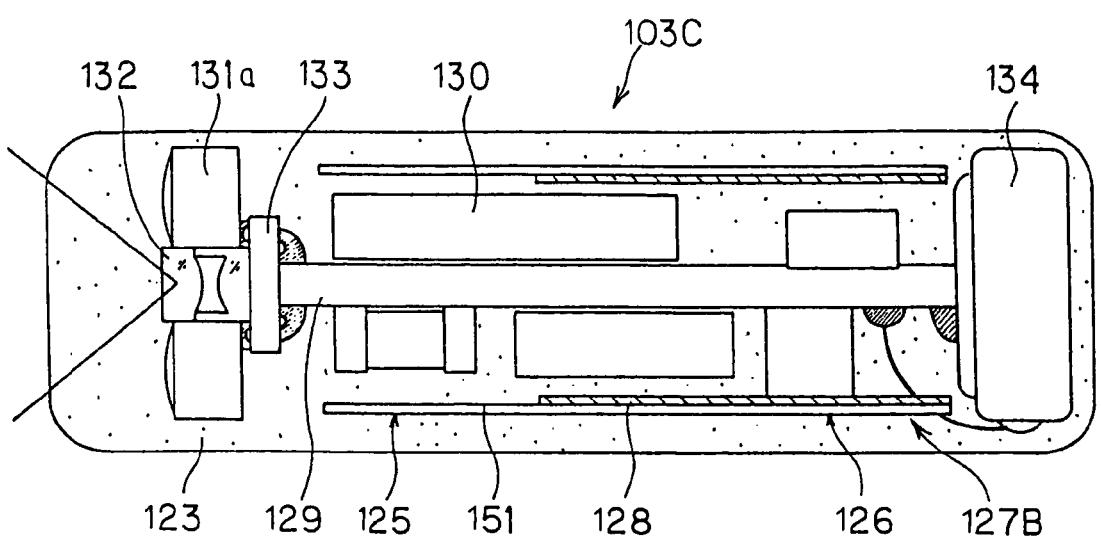

Referring to FIG. 21A, a capsule medical apparatus 103C according to the fifth embodiment comprises the flexible substrate 151 having the sending coil 125 and the power receiving coil 126 formed by printing patterns 152a and 152b (refer to FIG. 22A) that are cylindrically-shaped, in place of the coil core 124 in the capsule medical apparatus 103 shown in FIG. 18A.

Figure 22A:
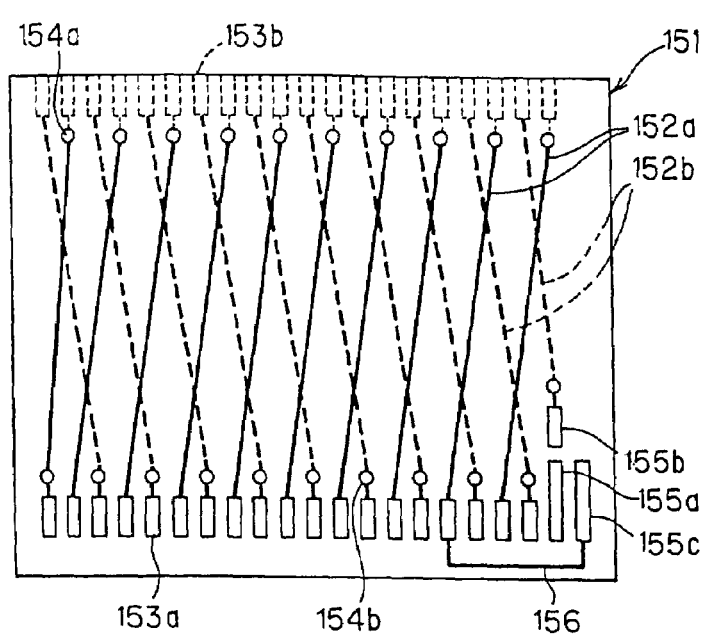
FIG. 22A is a diagram showing the structure of a flexible substrate.

Referring to FIG. 22A, the flexible substrate 151 is a square or rectangular thin-film before being molded into the cylindrical shape. A large number of printing patterns 152a and 152b are arranged linearly and in parallel to form the power receiving coil 126 and the sending coil 125 onto the front and rear surfaces of the flexible substrate 151.

Further, ends of the printing patterns 152a and 152b (on the top and bottom in FIG. 22A) are connected to electrode pads 153a and 153b arranged on the front and rear surfaces of the flexible substrate 151. In this case, one end of the printing pattern 152a on the front surface of the flexible substrate 151 is connected to the electrode pad 153 having the same array of pitches as that of the printing pattern 152a. The other end of the printing pattern 152a is connected to the electrode pad 153b via a through hole 154a.

One end of the printing pattern 152b on the rear surface of the flexible substrate 151 is connected to the electrode pad 153b having the same array of pitches as that of the printing pattern 152b. The other end of the printing pattern 152b is connected to the electrode pad 153a on the surface side via a through hole 154b.

Figure 22B:
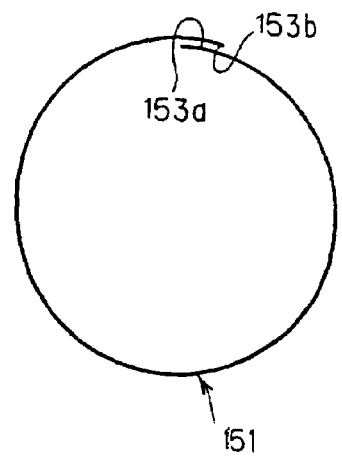
FIG. 22B is a diagram showing a cylindrical shape of the flexible substrate shown in FIG. 22A with its ends being connected.

The electrode pad 153b is formed to the end. However, the electrode pad 153a is formed to the slightly inner portion of the end. Referring to FIG. 22B, the flexible substrate 151 is cylindrically bent and the end on the rear surface is overlaid onto the portion near the end on the front surface, thereby overlaying and electrically connecting the electrode pad 153b on the rear surface to the electrode pad 153a on the front surface by soldering. Thus, the sending coil 125 and the power receiving coil 126 are formed.

The above-mentioned cylindrical electric connection forms one coil. According to the fifth embodiment, referring to FIG. 22A, three electrode pads 155a, 155b, and 155c are arranged near one end of the coil, thereby forming the sending coil 125 and the power receiving coil 126.

That is, referring to FIG. 22A, the two electrode pads 155a and 155b are arranged to be connected to both the ends of the coil. The electric pad 155c connected to the electrode pad 153a near the end of the coil via a printing pattern 156 (serving as a common electrode pad) is arranged.

The sending coil 125 comprises a coil having a printing pattern between the electrode pads 155a and 155c. The power receiving coil 126 comprises a coil having a printing pattern between the electrode pads 155b and 155c.

Figure 21B:
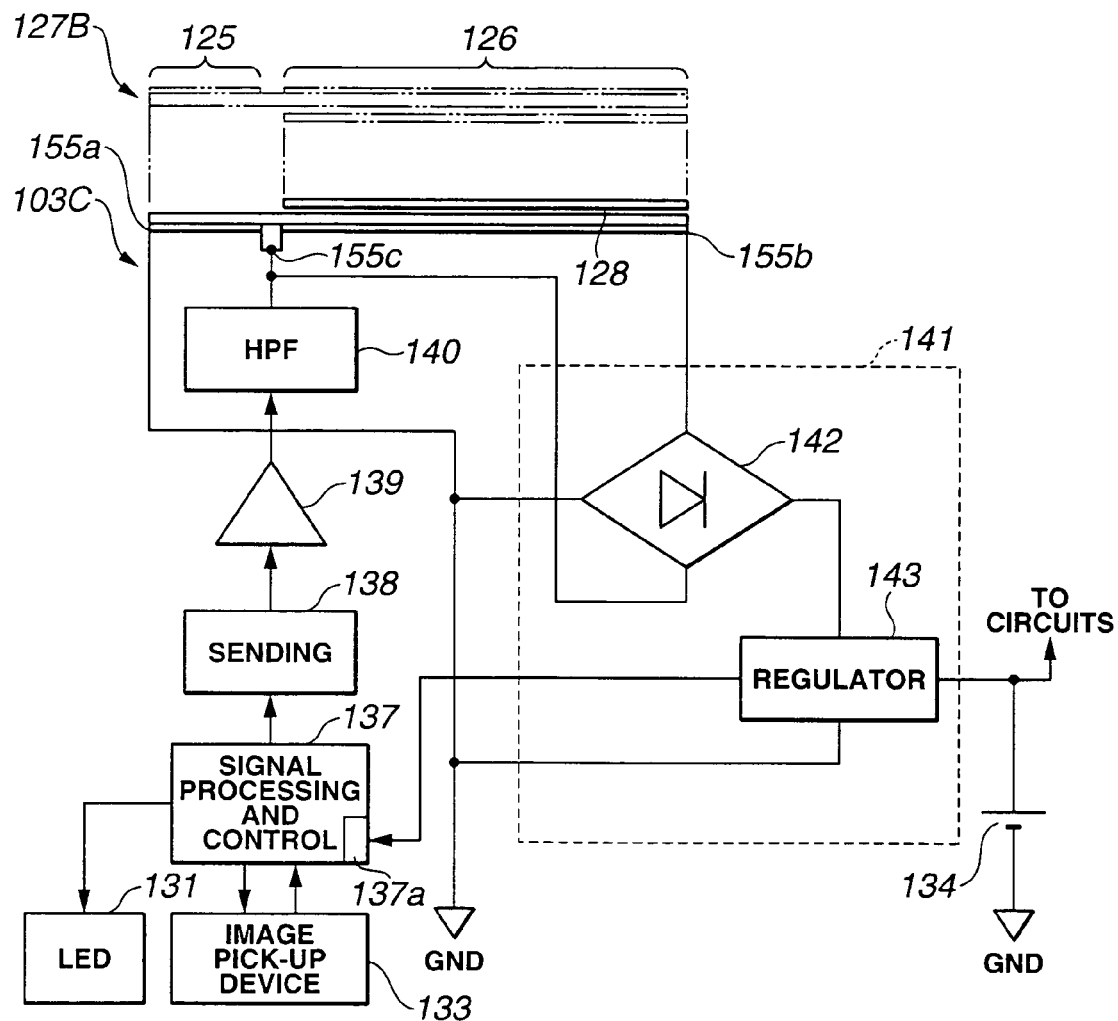
FIG. 21B is a diagram showing the structure of an electric system in the capsule medical apparatus.

FIG. 21B shows the structure of an electric system of the capsule medical apparatus 103C according to the fifth embodiment. Referring to FIG. 21B, the structure of the capsule medical apparatus 103C uses a coil member 127B containing the flexible substrate 151, in place of the coil member 127. Other structures are the same as the fourth embodiment.

According to the fifth embodiment, the coil member 127B comprises the sending coil 125 and the power receiving coil 126 with a smaller space as compared with the space according to the fourth embodiment.

Figure 23:
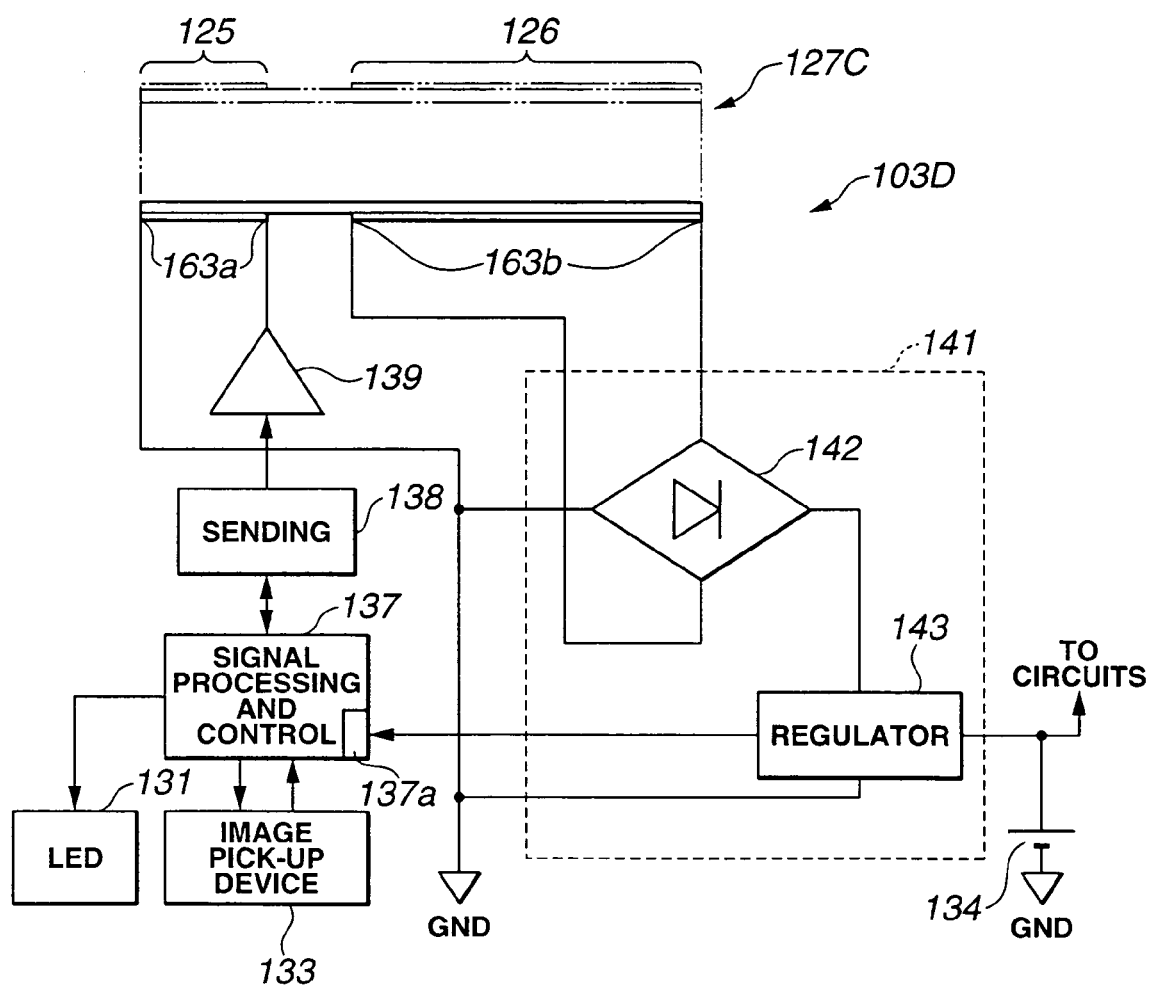

FIG. 23 shows the structure of an electric system of a capsule medical apparatus 103D according to a first modification. According to the first modification, the flexible substrate 151 is used. However, a coil member 127C is formed by separating the sending coil 125 and the power receiving 126 according to the first modification.

That is, referring to FIG. 24A, the flexible substrate 151 which is developed before cylindrical molding has a printing pattern 161 forming the sending coil 125 and a printing pattern 162 separately from each other in the axial direction (when the printing patterns 161 and 162 are in cylindrical shape). The printing patterns 161 and 162 contain the printing patterns 152a and 152b (although not designated by reference numerals in FIG. 24A, shown in FIG. 22A).

The ends of the printing patterns 161 and 162 are connected to electrode pads 163a and 163b.

According to the first modification, the single coil member 127C is formed by separating the sending coil 125 from the power receiving coil 126. Therefore, the HPF 140 shown in FIG. 21B is not necessary. That is, the structure of the electric system shown in FIG. 23 does not need the HPF 140 shown in FIG. 21B.

Other structures are the same as those shown in FIGS. 22A and 22B and have the same advantages as those in FIGS. 21A and 21B.

FIGS. 25A to 25C show a coil member 127D according to a second modification. FIG. 25A is a plan view of the coil member 127D which is developed in the two-dimensional direction. FIG. 25B is a sectional view showing the structure of the coil member 127D in the thickness direction. FIG. 25C is a diagram showing a state in which the coil member 127D is formed by cylindrically bending the coil member 127D and by connecting facing electrode pads.

According to the second modification, a multi-layer flexible substrate 171 comprises a printing pattern 172 forming the sending coil 125 on a first layer constituting the outer circumferential side, a conductive layer 173 which is formed (containing a conductive film) throughout a second layer constituting the inner side, and a printing pattern 174 forming the power receiving coil 126 constituting a third layer on the inner circumferential side.

In this case, referring to FIG. 25A, the outer shape of the conductive layer 173 is shown by a dotted line, and the conductive layer 173 serving as an intermediate layer approximately covers the half portion of the electrode pads 153b and 153a on both sides. A portion having the through holes 154a and 154b does not have the conductive film so as to prevent the short-circuit.

Referring to FIG. 25A, both the ends of the sending coil 125 comprising the printing pattern 172 become electrode pads 175a and 175b respectively. Both the ends of the power receiving coil 126 comprising the printing pattern 174 become electrode pads 176a and 176b respectively.

In this case, the electrode pad 175b is connected via a connecting pattern 177a, and the electrode pad 176b is connected via a connecting pattern 177b.

According to the second modification, the conductive layer 173 approximately covers the entire surface and is used for the ground. Consequently, the operation of a circuit system, which is arranged on the conductive layer 173, for picking-up the image and sending it, is stable. Further, the external noise is shielded and the influence thereof is reduced. Other structures have the same advantages as those in FIGS. 21A and 21B.

Figure 26:
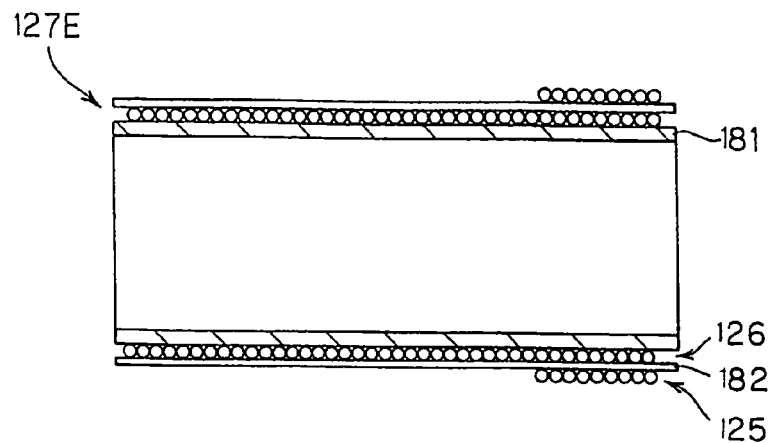

FIG. 26 shows a coil member 127E according to a third modification. In the coil member 127E, the power receiving coil 126 is constructed by winding the large number of coils out of a coil core 181 which is cylindrically-shaped. A conductive layer 182 is formed outside thereof by cylindrically winding cupper films. Further, the sending coil 125 is formed outside by winding the coils. The conductive layer 182 is used for the shielding similarly to the second modification.

The advantages in the case of using the coil member 127E are the same as those according to the second modification.

Figure 27A:
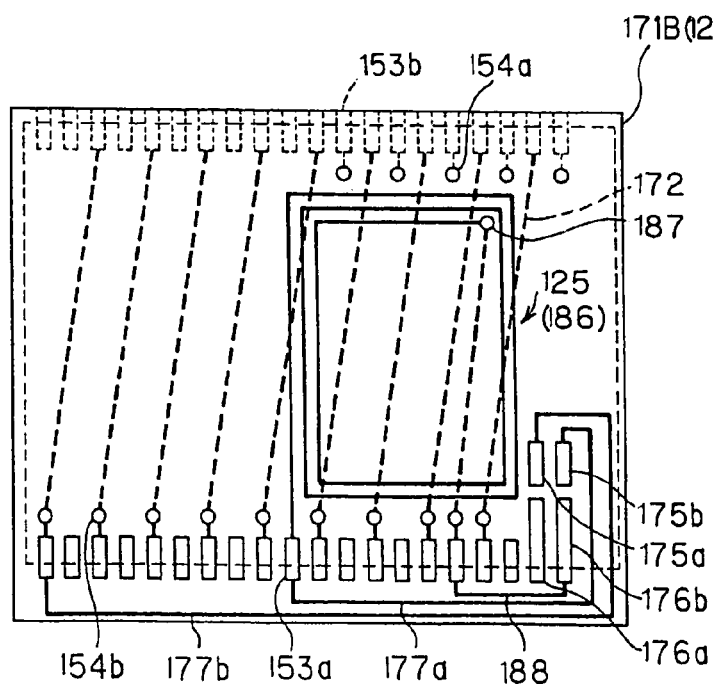
FIG. 27A is a diagram showing the structure of a flexible substrate constituting a coil member according to the fourth modification.
Figure 27B:
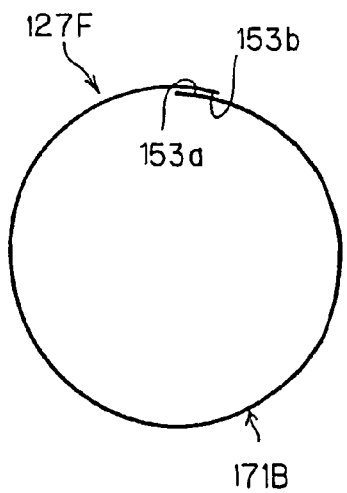

FIGS. 27A and 27B show a coil member 127F according to a fourth modification. Referring to the developed state in FIG. 27A, the coil member 127F according to the fourth modification contains a multi-layer flexible substrate 171B.

Referring to FIG. 25A, the sending coil 125 is formed by arranging the printing pattern 172 on the first layer of the flexible substrate 171 in parallel lines, similarly on the third layer. However, according to the fourth modification, a printing pattern 186 is rectangularly arranged on the first layer, thereby forming the sending coil 125.

One of ends rectangularly having the patterns on the inner side or outer side is connected to the electrode pad 153a, similarly to the case shown in FIG. 25A. The other end is connected to the electrode pad 153a via a through hole 187, the printing pattern 172 on the third-layer side, and the through hole 154b. Further, the other end is connected to the electrode pad 175a via a printing pattern 188 on the first-layer side.

Referring to FIG. 27B, the flexible substrate 171B is cylindrically bent and the facing electrode pads 153a and 153b are overlaid and are soldered, thereby forming the coil member 127F. Other structures are the same as those shown in FIGS. 25A and 25B. According to the fourth embodiment, the coil member 127D has the same advantages as those of the coil member 127D shown in FIGS. 25A and 25B.

Sixth Embodiment

Figure 28:
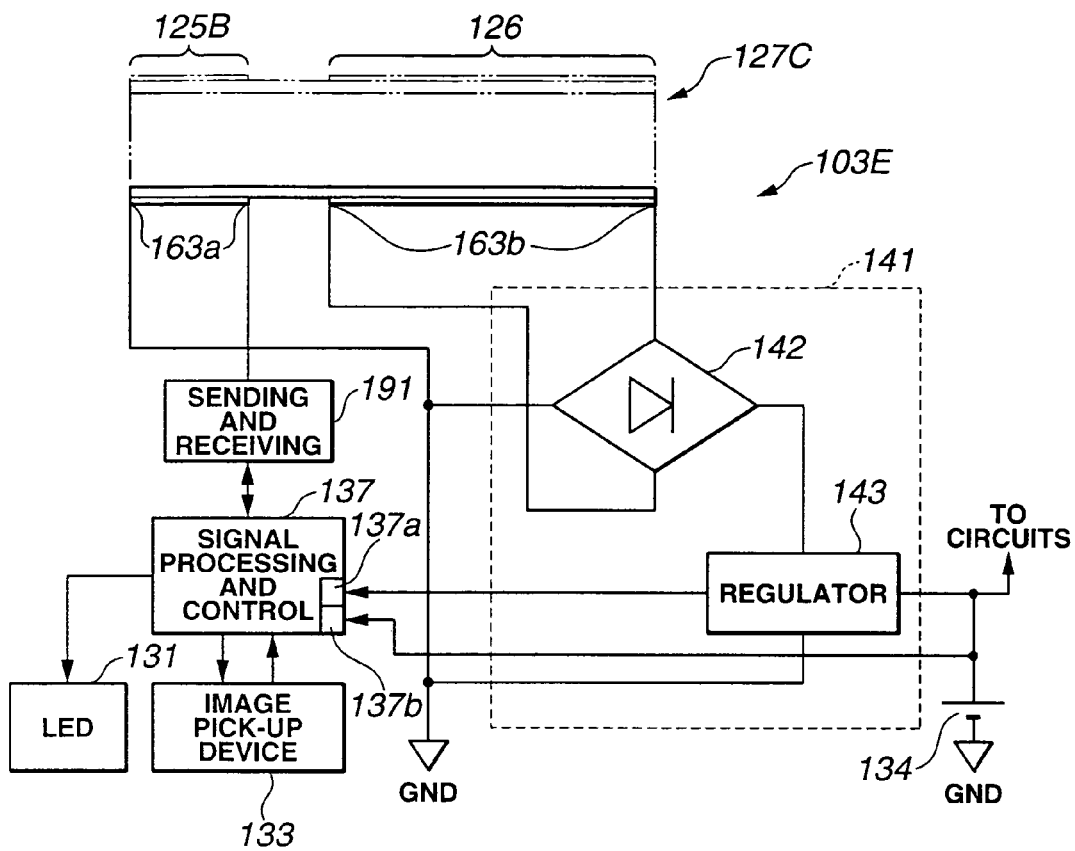
FIGS. 28 and 29 relate to a sixth embodiment of the present invention.

Next, a description is given of the sixth embodiment of the present invention with reference to FIG. 28. FIG. 28 shows the structure of an electric system of a capsule medical apparatus 103E according to the sixth embodiment. According to the sixth embodiment, in the structure shown in FIG. 23, a sending and receiving coil 125B shares the sending coil 125 for sending and receiving, and the sending and receiving coil 125B is connected to a sending and receiving circuit 191.

The sending and receiving circuit 191 is connected to the signal processing and control circuit 137. The sending and receiving circuit 191 receives the image data which is sent from the signal processing and control circuit 137. Further, the sending and receiving circuit 191 receives a control signal from the extracorporeal unit 105 side, then, demodulates the control signal, and outputs the demodulated signal to the signal processing and control circuit 137.

According to the sixth embodiment, a second voltage monitoring unit 137b for monitoring a voltage of the capacitor 134 is arranged. A signal detected by the second voltage monitoring unit 137b is outputted to the CPU in the signal processing and control circuit 137.

When the voltage of the capacitor 134 gets to a preset voltage of E1 or less, the CPU sends a power feed instructing signal via the sending and receiving circuit 191. When the voltage of the capacitor 134 gets to E2 or more, the CPU stops the sending of the power feed instructing signal.

The extracorporeal unit 105 receives information on the power feed instructing signal via the communication circuit 116 (refer to FIG. 17) and then sends the information to the control circuit 120 therein (refer to, FIG. 17). The control circuit 120 receives the power feed instructing signal and then activates the AC output circuit 119, thereby starting the power-feed operation.

Figure 29:
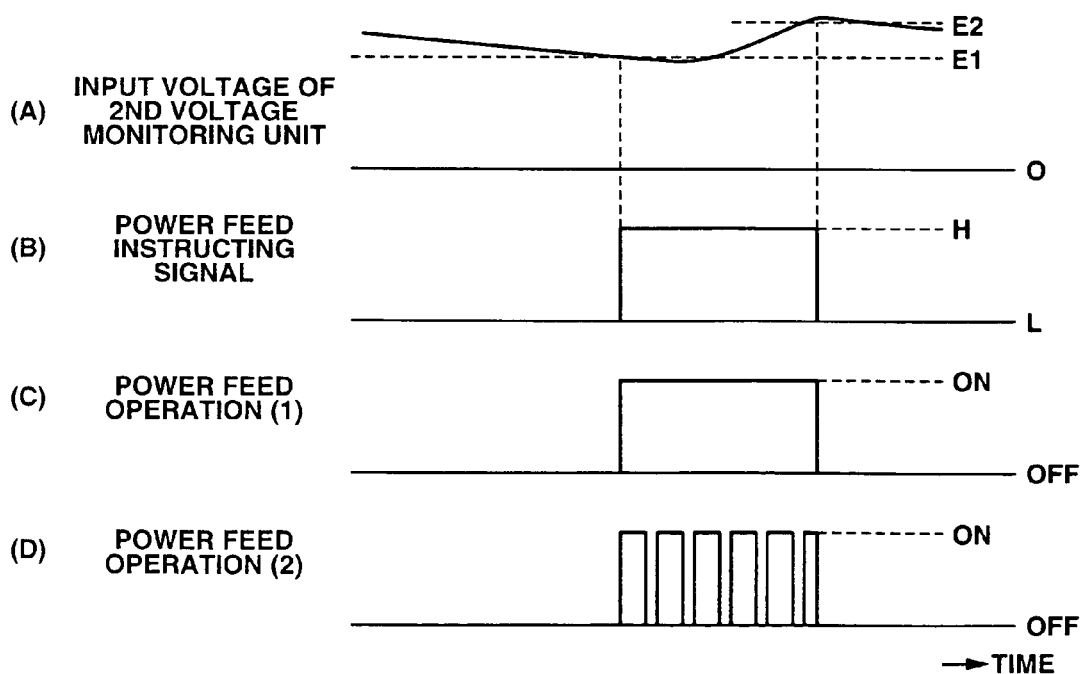

FIG. 29 shows a typical operation example according to the sixth embodiment. FIG. 29(A) shows an input voltage which is inputted to the second voltage monitoring unit 137b. Referring to FIG. 29(B), the CPU generates a power feed instructing signal when the input voltage gets to E1 or less.

The power feed instructing signal is sent by radio via the sending and receiving circuit 191 and the sending coil 125B. In the case of sending the normal image data, a code corresponding to the power feed instructing signal is added to the top or end portion of the image data and the resultant code is sent.

At the side of the extracorporeal unit 105, the control circuit 120 determines whether or not the code corresponding to the power feed instructing signal is added besides the image data.

The control circuit 120 determines that the power feed instructing signal is added. Then, the control circuit 120 sets the operating state of the AC output circuit 119, and starts the power feed operation as shown in FIG. 29(C).

In place of the power feed operation as shown in FIG. 29(C), the power feed operation may be intermittently started by operating the operating unit 115 in the extracorporeal unit 105 as shown in FIG. 29(D). In this case, upon stopping the power feed operation, the image data is sent.

The power feed operation increases a voltage to be charged to the capacitor 134. When the voltage gets to E2 or more, the power feed instructing signal is off, and the power feed operation stops.

According to the sixth embodiment, the energy state of the power feed means in the capsule medical apparatus 103E is monitored. When the power needs to be fed, the energy state is detected and the detecting signal is externally sent. The external device receives the detecting signal and the AC magnetic field for feeding the power is generated. Therefore, the power sending operation and the power receiving operation are properly performed.

DC power storing means for storing the DC power constituting the power feed circuit 141 is not limited to the capacitor 134 but may be a secondary battery such as a chargeable nickel hydride battery or a lithium-ion battery.

Further, when the secondary battery is provided and the electric energy of the secondary battery is consumed or the electric energy state becomes a state in which the power does not normally operate the electric system, a signal for externally feeding the power may be sent.

The information on the electric energy state of the secondary battery may externally be sent together with the image data. Further, the external extracorporeal unit 105 side may determine whether or not the power is to be fed and control the operation for generating or stopping the AC magnetic field.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule medical apparatus which generates power by radio using an AC magnetic field, the capsule medical apparatus comprising:
   a capsule-shaped casing; and
   a thin-film substrate which is arranged in the capsule casing,
   wherein a wiring is formed on the thin-film substrate such that a coil member having a power receiving coil for receiving the AC magnetic field and a sending coil for sending data outwards is constructed by cylindrically shaping the thin-film substrate, and
   a sending means for sending a signal from the capsule medical apparatus and a power feed circuit for supplying a power to the capsule medical apparatus are connected to the coil member.

2. The capsule medical apparatus according to claim 1, wherein the thin-film substrate is cylindrically shaped, and the outer diameter of the cylindrically shaped thin-film substrate substantially matches the outer diameter of the capsule casing.

3. The capsule medical apparatus according to claim 1, wherein the thin-film substrate is formed into a substantially polygonally-shaped-cylinder.

4. The capsule medical apparatus according to claim 1, wherein the thin-film substrate is formed into a substantially square-shaped-cylinder.

5. The capsule medical apparatus according to claim 1, wherein the wiring for the spiral coil formed onto the thin-film substrate has multi-layers.

6. The capsule medical apparatus according to claim 1, wherein a film containing a magnetic member is arranged to the inside of a coil wiring layer on the thin-film substrate that is cylindrically shaped.

7. The capsule medical apparatus according to claim 6, wherein the magnetic member is iron.

8. The capsule medical apparatus according to claim 6, wherein the magnetic member is permalloy.

9. The capsule medical apparatus according to claim 1, wherein a stick- or pipe-shaped magnetic member is arranged to the inside of the thin-film substrate that is cylindrically shaped.

10. The capsule medical apparatus according to claim 9, wherein the magnetic member is iron.

11. The capsule medical apparatus according to claim 9, wherein the magnetic member is permalloy.

12. A capsule medical apparatus which generates power by radio using an AC magnetic field, the capsule medical apparatus comprising:
  a capsule-shaped casing; and
  a squarely-shaped thin-film substrate which is arranged to the capsule casing,
    wherein a wiring is formed on the thin-film substrate such that a coil member having a power receiving coil for receiving the AC magnetic field and a sending coil for sending data outwards is constructed by connecting and cylindrically shaping two facing sides forming a part of the square shape of the thin-film substrate, and
    a sending means for sending a signal from the capsule medical apparatus and a power feed circuit for supplying power to the capsule medical apparatus are connected to the coil member.

13. The capsule medical apparatus according to claim 12, wherein the thin-film substrate is formed into a substantially square-shaped-cylinder.

14. The capsule medical apparatus according to claim 12, wherein the wirings on the two facing sides are electrically connected by soldering.

15. The capsule medical apparatus according to claim 12, wherein the wirings on the two facing sides are electrically connected by an anisotropic conductive film.

16. The capsule medical apparatus according to claim 12, wherein the shape of the thin-film substrate is substantially rectangular.

17. The capsule medical apparatus according to claim 12, wherein the shape of the thin-film substrate is substantially parallelogram.

18. The capsule medical apparatus according to claim 12, wherein the wiring for the spiral coil formed on the thin-film substrate have multi-layers.

19. The capsule medical apparatus according to claim 12, wherein a film containing a ferromagnetic member is arranged in the cylindrical inner surface of the thin-film substrate that is cylindrically shaped.

20. The capsule medical apparatus according to claim 12, wherein the two facing sides are wave-shaped like a rectangular wave, and the two sides are connected to be engaged with each other.

21. A capsule medical apparatus which generates power by radio using an AC magnetic field, the capsule medical apparatus comprising:
  a capsule-shaped casing; and
  a square thin-film substrate which is arranged in the capsule casing,
    wherein
      wirings are formed in the thin-film substrate such that a coil member having a power receiving coil for receiving the AC magnetic field and a sending coil for sending data outwards is constructed by connecting and cylindrically shaping two facing sides of a part of the square of the thin-film substrate,
      a sending means for sending a signal from the capsule medical apparatus and a power feed circuit for supplying power to the capsule medical apparatus are connected to the coil member, and
      the thin-film substrate comprises an electric part comprising at least one of the following: an illuminating circuit for controlling illuminating means for illumination, an image pick-up circuit for controlling image pick-up means for picking-up an image of a portion illuminated by the illuminating means, a commutating circuit for commutating generated current, charging means for charging generated power, a sending circuit for sending the picked-up signal by radio, and a control circuit for controlling the illuminating means and the illuminating circuit.

22. The capsule medical apparatus according to claim 21, wherein any of the circuits or a plurality of the circuits are mounted on the inner surface of the thin-film substrate that is cylindrically shaped.

23. The capsule medical apparatus according to claim 21, wherein any of the circuits or a plurality of the circuits are mounted on the outer surface of the thin-film substrate that is cylindrically shaped.

24. The capsule medical apparatus according to claim 21, wherein any of the circuits or a plurality of the circuits are mounted separately on the inner surface and the outer surface of the thin-film substrate that is cylindrically shaped.

25. The capsule medical apparatus according to claim 21, wherein the charging means is a capacitor.

26. The capsule medical apparatus according to claim 21, wherein the charging means is a ceramic capacitor.

27. The capsule medical apparatus according to claim 21, wherein the charging means is an electric double-layer capacitor.

28. The capsule medical apparatus according to claim 21, wherein the charging means is a secondary battery.

29. A capsule medical apparatus having a commutating circuit for generating AC power by an external AC magnetic field and converting the AC power into DC power, the capsule medical apparatus comprising:
  a capsule-shaped casing;
  a cylindrical thin-film substrate which is arranged in the capsule casing; and
  two or more pairs of coil members which are formed on the outer surface of the thin-film substrate,
  wherein
    each of the two or more pairs of coil members is further comprised of a power receiving coil for receiving the AC magnetic field and a sending coil for sending data outwards, and
    a sending means for sending a signal from the capsule medical apparatus and a power feed circuit for supplying power to the capsule medical apparatus are connected to the coil member.

30. The capsule medical apparatus according to claim 29, wherein the two or more pairs of coil members are formed in different directions.

31. The capsule medical apparatus according to claim 29, wherein an electro-magnetic part is mounted on the thin-film substrate.

32. A capsule medical system comprising a capsule medical apparatus inserted into the living body and an extracorporeal device for supplying electric energy by radio to the capsule medical apparatus from the outside of the living body,
  wherein
    the extracorporeal device comprises AC magnetic field generating means for generating an AC magnetic field, and the capsule medical apparatus comprises
a capsule-shaped casing;
a cylindrical thin-film substrate which is arranged in the capsule casing;
a coil member which is arranged onto the cylindrical thin-film substrate, the coil member having a power receiving coil for receiving the AC magnetic field and a sending coil for sending data outwards, and
a sending means for sending a signal from the capsule medical apparatus and a power feed circuit for supplying power to the capsule medical apparatus are connected to the coil member.

33. The capsule medical system according to claim 32, wherein the AC magnetic field generating means generates the AC magnetic field with a frequency band with low attenuation in the living body.

34. The capsule medical system according to claim 32, wherein the AC magnetic field generating means generates the AC magnetic field with the frequency of 150 kHz or less.

35. A capsule medical apparatus for sending data to the outside and receiving power from the outside, comprising:
a sending antenna for sending the data; and
a power receiving antenna for receiving the supplied power,
wherein
the sending antenna and the power receiving antenna are formed as a single coil member, and
a sending means for sending a signal from the capsule medical apparatus and a power feed circuit for supplying power to the capsule medical apparatus are connected to the coil member.

36. The capsule medical apparatus according to claim 35, wherein the coil member is formed onto a flexible substrate.

37. The capsule medical apparatus according to claim 35, wherein the sending antenna and the receiving antenna are arranged onto the same substrate.

38. The capsule medical apparatus according to claim 35, wherein the sending antenna and the receiving antenna are arranged onto the same flexible substrate, and the flexible substrate is substantially cylindrically shaped.

39. The capsule medical apparatus according to claim 35, wherein the power receiving antenna is coil-shaped, a shielding layer containing a conductive member is formed to the outside of the power receiving antenna, and further the sending antenna is arranged to the outside of the shielding layer.

40. The capsule medical apparatus according to claim 35, wherein the sending means and the power feed circuit are driven by different frequencies.

41. The capsule medical apparatus according to claim 35, wherein the sending means and the power feed circuit are driven at different times.

42. The capsule medical apparatus according to claim 35, wherein the coil member has an intermediate electrode, and the sending means is connected to the intermediate electrode.

43. The capsule medical apparatus according to claim 35, wherein the coil member has an intermediate electrode, and the sending means and the power feed circuit are connected to the intermediate electrode.

44. The capsule medical apparatus according to claim 35, wherein a filter for removing a signal of a frequency band from the power feed circuit is arranged between the sending means and the coil member.

45. The capsule medical apparatus according to claim 35, further comprising:
means for monitoring the charged power in the power feed circuit.

46. A capsule medical apparatus which generates power by radio using an AC magnetic field, the capsule medical apparatus comprising:
a capsule-shaped casing; and
a thin-film substrate which is arranged in the capsule casing,
wherein
a wiring is formed on the thin-film substrate such that a spiral coil for receiving the AC magnetic field is constructed by cylindrically shaping the thin-film substrate, and
the wiring for the spiral coil formed onto the thin-film substrate has multi-layers.

47. A capsule medical apparatus which generates power by radio using an AC magnetic field, the capsule medical apparatus comprising:
a capsule-shaped casing; and
a squarely-shaped thin-film substrate which is arranged to the capsule casing,
wherein
a wiring is formed on the thin-film substrate such that a spiral coil for receiving the AC magnetic field is constructed by connecting the cylindrically shaping two facing sides forming a part of the square shape of the thin-film substrate, and
the wirings on the two facing sides are electrically connected by an anisotropic conductive film.

48. A capsule medical apparatus which generates power by radio using an AC magnetic field, the capsule medical apparatus comprising:
a capsule-shaped casing; and
a squarely-shaped thin-film substrate which is arranged to the capsule casing,
wherein
a wiring is formed on the thin-film substrate such that a spiral coil for receiving the AC magnetic field is constructed by connecting the cylindrically shaping two facing sides forming a part of the square shape of the thin-film substrate, and
the wiring for the spiral coil formed on the thin-film substrate have multi-layers.

49. A capsule medical apparatus which generates power by radio using an AC magnetic field, the capsule medical apparatus comprising:
a capsule-shaped casing; and
a squarely-shaped thin-film substrate which is arranged to the capsule casing,
wherein
a wiring is formed on the thin-film substrate such that a spiral coil for receiving the AC magnetic field is constructed by connecting the cylindrically shaping two facing sides forming a part of the square shape of the thin-film substrate, and
the two facing sides are wave-shaped like a rectangular wave, and the two sides are connected to be engaged with each other.

50. A capsule medical apparatus for sending data to the outside and receiving power from the outside, comprising:
a sending antenna for sending the data; and
a power receiving antenna for receiving the supplied power,
wherein
the sending antenna and the power receiving antenna are formed on a coil member, and
the power receiving antenna is coil-shaped, a shielding layer containing a conductive member is formed to the outside of the power receiving antenna, and further the sending antenna is arranged to the outside of the shielding layer.

* * * * *

UNITED STATES PATENT AND TRADEMARK OFFICE
CERTIFICATE OF CORRECTION

PATENT NO. : 7,604,591 B2 Page 1 of 1
APPLICATION NO. : 10/974486
DATED : October 20, 2009
INVENTOR(S) : Uchiyama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1371 days.

Signed and Sealed this

Fourteenth Day of December, 2010

David J. Kappos
*Director of the United States Patent and Trademark Office*